(12) United States Patent
Aubin et al.

(10) Patent No.: US 7,585,637 B2
(45) Date of Patent: Sep. 8, 2009

(54) ESTROGEN RELATED RECEPTOR, ERRα, A REGULATOR OF BONE FORMATION

(76) Inventors: Jane Aubin, 643 Pape Avenue, Toronto, Ontario (CA) M5K 3S2; Edith Bonnelye, 33 rue Leo et Maurice Trouilhet 3eme etage, 69008 Lyon (FR)

( * ) Notice: Subject to any disclaimer, the term of this patent is extended or adjusted under 35 U.S.C. 154(b) by 0 days.

(21) Appl. No.: 11/438,172

(22) Filed: May 22, 2006

(65) Prior Publication Data
US 2006/0211049 A1   Sep. 21, 2006

Related U.S. Application Data

(62) Division of application No. 10/089,429, filed as application No. PCT/CA00/01015 on Aug. 30, 2000, now abandoned.

(30) Foreign Application Priority Data
Sep. 30, 1999   (CA) .................................. 2284103

(51) Int. Cl.
*G01N 33/53*     (2006.01)
*C12N 5/00*      (2006.01)
*C07K 14/72*     (2006.01)
(52) U.S. Cl. .................... 435/7.1; 435/325; 530/350
(58) Field of Classification Search .................. None
See application file for complete search history.

(56) References Cited

U.S. PATENT DOCUMENTS

| | | | |
|---|---|---|---|
| 5,571,696 A | 11/1996 | Evans et al. | 435/69.1 |
| 5,710,004 A | 1/1998 | Evans et al. | 435/6 |
| 5,840,690 A | 11/1998 | Holick | 514/12 |

OTHER PUBLICATIONS

Bellows et al. Expression of mRNAs for type-1 collagen, bone sialoprotein, osteocalcin, and osteopontin at different stages of osteoblastic differentiation and their regulation by 1,25 dihydroxyvitamin D3. Cell Tissue and Research vol. 297:249-259 (Jul. 1999).*

Yeh et al. Osteogenic protein-1 regulates insulin-like growth (IGF-1), IGF-11, and IGF-binding protein-5 (IGFBP-5) gene expression in fetal rat calvaria cells by different mechanisms. Journal of Cellular Physiology 175:78-88 (1998).*

Aubin, JE. et al., The Osteoblast Lineage, (1996), Principles of Bone Biology, Academic Press, San Diego, pp. 51-67.

Bonnelye, E. et al., The ERR-1 Orphan Receptor is a Transcriptional Activator Expressed During Bone Development, (1997), Mol Endocrinol, v.11, pp. 905-916.

Bonnelye, E. et al. Expression of the estrogen-related receptor 1 (ERR-1) orphan receptor during mouse development, (1997) Mechanisms of Development, v. 65, pp. 71-85.

Bonnelye E et al., The Orphan Receptor, Estrogen Related Receptor EERα, is Differentially Expressed during Osteoblast Development and Regulates Bone Formation, (1999), Journal of Bone and Mineral Research, v. 14, p. S193.

Braidman, JP. et al., Preliminary In Situ Identification of Estrogen Target Cells in Bone, (1995), Journal of Bone and Mineral Research, v. 10, pp. 74-80.

Buckley,MF. et al., Expression and amplification of cyclin genes in human breast cancer, (1993), Oncogene, v. 8, pp. 2127-2133.

Enmark,E et al., Orphan Nuclear Receptors-The First Eight Years, (1996), Mol.Endocrinol., v.10, pp. 1293-1307.

Giguère V. et al., Identification of a new class of steroid hormone receptor, (1988), Nature v. 331, pp. 91-94.

Gronemeyer H. et al., Transcription factors 3: nuclear receptors; Protein profile, (1995), v. 2, pp. 1173-1308.

Harris,SA. et al., Estrogens and Progestins, (1996), Principles of Bone Biology. Academic Press, San Diego, pp. 507-520.

Hong,H. et al., Hormone-independent Transcriptional Activation and Coactivator Binding by Novel Orphan Nuclear Receptor ERR3, (1999), J. Biol. Chem, v. 274 (32), pp. 22618-22626.

Hoyland,JA. et al., Effect of Ovarian Steroid Deficiency on Oestrogen Receptor α Expression in Bone, (1999), Journal of Pathology, v. 188 (3), pp. 294-303.

Johnston,S.D., et al., Estrogen-Related Receptor α1 Functionally Binds as a Monomer to Extended Half-Site Sequences Including Ones Contained Within Estrogen-Response Elements, (1997), Molecular Endocrinology, v. 11, pp. 342-352.

Korach,K.S. Insights from the Study of Animals Lacking Functional Estrogen Receptor, (1994), Science, v. 266, pp. 1524-1527.

Kuiper,G.G.JM. et al., Cloning of a novel estrogen receptor expressed in rat prostate and ovary, (1996), Proc.Natl Acad. Sci. USA, v. 93, pp. 5925-5930.

Ben-Hur et al., "Localization of Estrogen Receptors in Long Bones and Vertebrae of Human Fetuses," *Calcif Tissue Int* 53 91-96: (1993).

Denhardt et al., "Osteopontin Expression and Function: Role in Bone Remodeling," *Journal of Cellular Biochemistry Supplements* 30(31): 92-102 (1998).

Eriksen et al., "Evidence of Estrogen Receptors in Normal Human Osteoblast-Like Cells," *Science* 241 (84-86).

Pettersson et al., "Expression of a novel member of estrogen response element-binding nuclear receptors is restricted to the early stages of chorion formation during mouse embryogenesis," *Mechanisms of Development* 54:211-223 (1996).

Shi et al., "Human Estrogen Receptor-Like 1 (ESRL1) Gene: Genomic Organization, Chromosomal Localization, and Promoter Characterization," *Genomics* 44: 52-60 (1997).

Yang et al., "Modulation of Aromatase Expression in the Breast Tissue by ERRα-1 Orphan Receptor," *Cancer Research* 38: 5695-5700 (Dec. 15, 1998).

Yang et al., "Two Organochlorine Pesticides, Toxaphene and Chlordane, Are Antagonists for Estrogen-related Receptor α-1 Orphan Receptor," *Cancer Research* 59: 4519-4524 (Sep. 15, 1999).

(Continued)

*Primary Examiner*—Marianne P Allen
*Assistant Examiner*—Regina M DeBerry
(74) *Attorney, Agent, or Firm*—Myers Bigel Sibley & Sajovec P.A.

(57) ABSTRACT

Methods and pharmaceutical compositions are provided for modulating bone formation in a mammal. Methods are also provided for screening compounds for their efficacy as modulators of bone formation.

8 Claims, 12 Drawing Sheets

OTHER PUBLICATIONS

Komm, BS, et al., Estrogen Binding, Receptor mRNA, and Biologic Response in Osteoblast-Like Osteosarcoma Cells, (1988), Science, v. 241, pp. 81-83.

Malaval, L., et al., Kinetics of Osteoprogenitor Proliferation and Osteoblast Differentiation In Vitro, (1999), J. Cell. Biochem., v. 74, pp. 616-627.

Onoe,Y, et al., Expression of Estrogen Receptor β in Rat Bone, (1997), Endocrinology, v. 138, No. 10, pp. 4509-4512.

Pacifici, R., Estrogen, Cytokines, and Pathogenesis of Postmenopausal Osteoporosis, (1996), Journal of Bone and Mineral Research, v. 11, No. 8, pp. 1043-1051.

Sabbah,M, et al., Estrogen induction of the cyclin D1 promoter: Involvement of a cAMP response-like element, (1999), Proc Natl. Acad. Sci., v. 96, pp. 11217-11222.

Shigeta, H., et al., The mouse estrogen receptor-related orphan receptor α1: molecular cloning and estrogen responsiveness, (1997), Journal of Molecular Endocrinology, v. 19, pp. 299-309.

Sladek,R., et al., The Orphan Nuclear Receptor Estrogen-Related Receptor α Is a Transcriptional Regulator of the Human Medium-Chain Acyl Coenzyme A Dehydrogenase Gene, (1997), Mol.Cell. Biol., v. 17, pp. 5400-5409.

Turner RT, et al., Skeletal Effects of Estrogen, (1994), Endocrine Reviews, v. 15, pp. 275-300.

Vanacker,J.-M. et al., Transcriptional targets shared by estrogen receptor-related receptors (ERRs) and estrogen receptor (ER) α, but not by Erβ, (1999),The EMBO Journal v. 18, pp. 4270-4279.

Vanacker,J.-M. et al., Activation of the Osteopontin Promoter by the Orphan Nuclear Receptor Estrogen Receptor Related $\alpha^1$, (1998), Cell Growth Differ., v. 9, pp. 1007-1014.

Vanderschueren et al., Aromatization of Androgens is Important for Skeletal Maintenance of Aged Male Rats, (1996), pp. 179-183.

Vega, RB., et al., A Role for Estrogen-related Receptor α in the Control of Mitochondrial Fatty Acid β-Oxidation during Brown Adipocyte Differentiation, (1997), Journal of Biological Chemistry, v. 272, pp. 31693-31699.

Wiley SR, et al., SV40 early-to-late switch involves titration of cellular transcriptional repressors, (1993), Genes and Development, v. 7, pp. 2206-2219.

Windahl,SH, et al., Increased cortical bone mineral content but unchanged trabecular bone mineral density in female *ERβ-/-* mice, (1999), Journal of Clinical Investigation, v. 104, pp. 895-901.

Windahl,SH, et al., Cellular Distribution of Estrogen Receptor β in Neonatal Rat Bone, (2000), Bone, v. 26, pp. 117-121.

Yang N. et al., Estrogen-related Receptor, hERR1, Modulates Estrogen Receptor-mediated Response of Human Lactoferrin Gene Promoter, (1996), J. Biol. Chem. v. 271, pp. 5795-5804.

Zhang,Z., et al., Estrogen Receptor-related Receptor α1 Interacts with Coactivator and Constitutively Activates the Estrogen Response Elements of the Human Lactoferrin Gene, (2000), J. Biol. Chem., v. 275, pp. 20837-20846.

\* cited by examiner

A Femur

Subcutaneous injections of 17β-estradiol (500μg/animal/week)

B Flushed bones

Subcutaneous injections of 17β-estradiol (500μg/animal/week)

SEQUENCE LISTING

```
<160> NUMBER OF SEQ ID NOS: 30

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
caggaaagtg aatgcccagg                                               20

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
ctttgcagca aatatacatt                                               20

<210> SEQ ID NO 3
<211> LENGTH: 23
<212> TYPE: DNA
<213> ORGANISM: Artificial sequence
<220> FEATURE:
<223> OTHER INFORMATION: Primer

<400> SEQUENCE: 3
gagctgccaa cctttggcca agt                                           23

<210> SEQ ID NO 4
<211> LENGTH: 21
<212> TYPE: DNA
<213> ORGANISM: Artificial sequence
<220> FEATURE:
<223> OTHER INFORMATION: Primer

<400> SEQUENCE: 4
```

```
tgaacttgat cgtggagatt c                                              21

<210> SEQ ID NO 5
<211> LENGTH: 24
<212> TYPE: DNA
<213> ORGANISM: Artificial sequence
<220> FEATURE:
<223> OTHER INFORMATION: Primer

<400> SEQUENCE: 5
aaagccaaga gaaacggtgg gcat                                           24

<210> SEQ ID NO 6
<211> LENGTH: 24
<212> TYPE: DNA
<213> ORGANISM: Artificial sequence
<220> FEATURE:
<223> OTHER INFORMATION: Primer

<400> SEQUENCE: 6
gccaatcatg tgcaccagtt cctt                                           24

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
catggctgcc cttcggcctc                                                20

<210> SEQ ID NO 8
<211> LENGTH: 21
<212> TYPE: DNA
<213> ORGANISM: Artificial sequence
<220> FEATURE:
<223> OTHER INFORMATION: Primer

<400> SEQUENCE: 8
cattctcttc gctgcgtagc c                                              21

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
aggaccctct ctctgctcac                                                20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
aacggtggtg ccatagatgc                                                20

<210> SEQ ID NO 11
<211> LENGTH: 22
<212> TYPE: DNA
<213> ORGANISM: Artificial sequence
```

```
<220> FEATURE:
<223> OTHER INFORMATION: Primer

<400> SEQUENCE: 11
cgcctacttt tatcctcctc tg                                              22

<210> SEQ ID NO 12
<211> LENGTH: 22
<212> TYPE: DNA
<213> ORGANISM: Artificial sequence
<220> FEATURE:
<223> OTHER INFORMATION: Primer

<400> SEQUENCE: 12
ctgaccctcg tagccttcat ag                                              22

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
cccgcatcct taagggccag                                                 20

<210> SEQ ID NO 14
<211> LENGTH: 19
<212> TYPE: DNA
<213> ORGANISM: Artificial sequence
<220> FEATURE:
<223> OTHER INFORMATION: Primer

<400> SEQUENCE: 14
taggcgatgt ccttgcagc                                                  19

<210> SEQ ID NO 15
<211> LENGTH: 19
<212> TYPE: DNA
<213> ORGANISM: Artificial sequence
<220> FEATURE:
<223> OTHER INFORMATION: Primer

<400> SEQUENCE: 15
gccacttggc tgaagcctg                                                  19

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
gaaactcctg gactttgacc                                                 20

<210> SEQ ID NO 17
<211> LENGTH: 19
<212> TYPE: DNA
<213> ORGANISM: Artificial sequence
<220> FEATURE:
<223> OTHER INFORMATION: Primer

<400> SEQUENCE: 17
cttcattcgc ctcacaaac                                                  19
```

```
<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
cacgtcgctc atcttgccgg                                              20

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
tcccgccagc agcaagacac                                              20

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
tgagcttgtt caccagaagc                                              20

<210> SEQ ID NO 21
<211> LENGTH: 20
<212> TYPE: DNA
<213> ORGANISM: Artificial sequence
<220> FEATURE:
<223> OTHER INFORMATION: Primer

<400> SEQUENCE: 21
atagagccgg cggagccgcg                                              20

<210> SEQ ID NO 22
<211> LENGTH: 20
<212> TYPE: DNA
<213> ORGANISM: Artificial sequence
<220> FEATURE:
<223> OTHER INFORMATION: Primer

<400> SEQUENCE: 22
aagccccggt cgacggggtg                                              20

<210> SEQ ID NO 23
<211> LENGTH: 20
<212> TYPE: DNA
<213> ORGANISM: Artificial sequence
<220> FEATURE:
<223> OTHER INFORMATION: Primer

<400> SEQUENCE: 23
ccttggagca gccgccccag                                              20

<210> SEQ ID NO 24
<211> LENGTH: 21
<212> TYPE: DNA
<213> ORGANISM: Artificial sequence
<220> FEATURE:
<223> OTHER INFORMATION: Primer
```

<400> SEQUENCE: 24
atgtgggcgt cccgaagtag g    21

<210> SEQ ID NO 25
<211> LENGTH: 20
<212> TYPE: DNA
<213> ORGANISM: Artificial sequence
<220> FEATURE:
<223> OTHER INFORMATION: Primer

<400> SEQUENCE: 25
ggggaaacac cagaatcaag    20

<210> SEQ ID NO 26
<211> LENGTH: 20
<212> TYPE: DNA
<213> ORGANISM: Artificial sequence
<220> FEATURE:
<223> OTHER INFORMATION: Primer

<400> SEQUENCE: 26
agagaagtca tccccagccc    20

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
ggagagagtg ccaactccag    20

<210> SEQ ID NO 28
<211> LENGTH: 20
<212> TYPE: DNA
<213> ORGANISM: Artificial sequence
<220> FEATURE:
<223> OTHER INFORMATION: Primer

<400> SEQUENCE: 28
ccaccccagg gataaaaact    20

<210> SEQ ID NO 29
<211> LENGTH: 16
<212> TYPE: PRT
<213> ORGANISM: Rattus norvegicus

<400> SEQUENCE: 29

Asn His Cys Pro Ala Ser Asp Glu Cys Glu Ile Thr Lys Arg Arg Cys
1               5                   10                  15

<210> SEQ ID NO 30
<211> LENGTH: 20
<212> TYPE: DNA
<213> ORGANISM: Antisense sequence

<400> SEQUENCE: 30
tcaccggggg ttcagtctca    20

ESTROGEN RELATED RECEPTOR, ERRα, A REGULATOR OF BONE FORMATION

RELATED APPLICATION INFORMATION

This application is a divisional of U.S. application Ser. No. 10/089,429, filed Nov. 29, 2002 now abandoned, which claims the benefit under 35 U.S.C. §371 from PCT Application No. PCT/CA00/01015, filed Aug. 30, 2000, which claims the benefit of Canadian Application Serial No. 2,284,103, filed Sep. 30, 1999, the disclosures of which are incorporated by reference herein in their entireties.

FIELD OF THE INVENTION

The present invention relates to methods and pharmaceutical compositions for modulation of bone formation.

BACKGROUND OF THE INVENTION

In the description which follows, references are made to certain literature citations which are listed at the end of the specification and all of which are incorporated herein by reference.

Nuclear receptors are transcription factors involved in various physiological regulatory processes. The superfamily to which nuclear receptors belong comprises both ligand-dependent molecules such as the steroid hormone-, thyroid hormone-, retinoic acid- and vitamin D-receptors, and an increasing number of so-called orphan receptors for which no ligand has yet been determined (Gronemeyer H, Laudet V., 1995; Enmark and Gustafsson, 1996). Indeed, it is not yet known whether the orphan receptors have ligands that await identification or whether they act in a constitutive manner. The orphan receptors display the same structural organization as do the classic ligand-dependent receptors: the A/B domain located in the N-terminal part of the protein harbors a ligand-independent transactivation function (AF-1); the C domain, which is the most conserved part of the molecule, is responsible for the specific DNA-binding activity; the E domain contains the ligand binding hydrophobic pocket and contributes to receptor dimerization and to the ligand-dependent transactivation function (AF-2).

Two orphan receptors, estrogen receptor-related receptor α (ERRα) and ERRβ (Giguere et al., 1988; NR3B1 and NR3B2, respectively, according to the Nuclear Receptors Nomenclature Committee, 1999) are closely related to the estrogen receptors ERα and ERβ (Green et al., 1986; Kuiper et al., 1996; NR3A1 and NR3A2 respectively). ERRα (Genbank Accession No. for human ERRα: NM_004451) and ERRβ were identified by low-stringency screening of cDNA libraries with a probe encompassing the DNA-binding domain of the human estrogen receptor (ER). Recently, a third estrogen receptor-related receptor, ERR3 or ERRγ, was identified by yeast two-hybrid screening with the glucocorticoid receptor interacting protein 1 (GRIP1) as bait (Hong et al, 1999). The DNA binding domain region of ERRs and ERs is highly conserved, however the others parts of the protein share very little homology (Giguere et al, 1988; Hong et al, 1999). Therefore, sequence alignment of ERRα and the ERs reveals a high similarity (68%) in the 66 amino acids of the DNA-binding domain and a moderate similarity (36%) in the ligand-binding E domain, which may explain the fact that ERRα does not bind estrogen. Although ligands for the ERRs have not been clearly identified, the pesticides chlordane and toxaphene have been suggested to be potential ligands for ERRα (Yang and Chen, 1999). ERRα has been identified as a regulator of the SV40 major late promoter during the early-to-late switch of expression (Wiley et al., 1993) and as a regulator of fat metabolism (Sladek et al., 1997; Vega et al, 1997). Yang et al. also showed that ERR modulates the activating effect of estrogens on the lactoferrin promoter and suggested that ERRα may interact with ERs through protein-protein interaction (Yang et al., 1996; Zhang and Teng, 2000). Finally, ERRα has been described as a modulator of the human aromatase gene in breast, and hypothesized to be critical for normal breast development and to play an important role in the pathogenesis and maintenance of breast cancer via its ability to interact with ERs (Yang et al, 1998).

Postmenopausal osteoporosis is a condition caused primarily by the severe decrease of serum estrogen levels after cessation of ovarian function. The absence of estrogen results in an increase in bone turnover (Turner et al, 1994) and a negative bone remodeling balance, leading to bone loss and an increased fracture risk. An anabolic effect of estrogens on bone homeostasis has been documented in post-menopausal osteoporosis (for review see Pacifi, 1996), where bone loss can be reversed by administration of natural or synthetic estrogens. Although the bone preserving effect of estrogen replacement is indisputable, the molecular and cellular mechanism of action for this hormone effect remain unclear. ERs are expressed in osteoblasts (Turner et al., 1994; Eriksen et al, 1988; Komm et al, 1988), and estrogens have been found to elicit effects ranging from modulation of gene expression to regulation of proliferation in this cell type (for review Harris et al, 1996). In contrast, mice lacking a functional ERα or ERβ have only minor skeletal abnormalities (Korach et al, 1994; Windahl et al, 1999) suggesting that other mechanisms or receptors might be important during skeletal development. ERRβ expression is restricted to early development and to a few adult tissues (Giguere et al., 1988; Pettersson et al., 1996). In contrast, ERRα has a broader spectrum of expression, including fat, muscle, brain, testis and skin (Bonnelye et al, 1997b). Strikingly, ERRα is also highly expressed in the ossification zones of the mouse embryo (in long bones, vertebrae, ribs and skull), and is more widely distributed in osteoblast-like cells than is ERα (Bonnelye et al., 1997a). Moreover it has been shown that ERRα positively regulates the osteopontin gene (Vanacker et al, 1998), an extracellular matrix molecule secreted by osteoblasts and other cells and thought to play a role in bone remodelling among other functions (Denhardt and Noda, 1998).

SUMMARY OF THE INVENTION

The inventors have demonstrated the involvement of ERRα in the modulation of bone formation in mammals. Up regulation of ERRα increased osteoblast differentiation from progenitor cells and also proliferation of progenitor cells. Down regulation of ERRα caused inhibition of bone formation, with reduction of osteoblast numbers and differentiation. ERRα was shown to be expressed also in osteocytes in both calvaria and long bones, indicating a role in skeletal maintenance.

In accordance with one embodiment of the present invention, a method of increasing proliferation of osteoblasts in a mammal comprises administering to the mammal an effective amount of an agent selected from the group consisting of:

(a) an estrogen related receptor alpha (ERRα) agonist;

(b) a substantially purified ERRα protein; and (c) a nucleotide sequence encoding ERRα protein.

(d) an agent which enhances expression of a gene encoding an ERRα protein.

In accordance with another embodiment of the present invention, a method of increasing differentiation of osteoblasts in a mammal comprises administering to the mammal an effective amount of an agent selected from the group consisting of:
(a) an ERRα agonist;
(b) a substantially purified ERRα protein; and
(c) a nucleotide sequence encoding ERRα protein.
(d) an agent which enhances expression of a gene encoding an ERRα protein.

In accordance with another embodiment of the present invention, a method of reducing proliferation of osteoblasts in a mammal comprises administering to the mammal an effective amount of an agent selected from the group consisting of:
(a) an ERRα antagonist;
(b) a purified antibody which binds specifically to an ERRα protein;
(c) an antisense nucleotide sequence complementary to and capable of hybridizing to a nucleotide sequence encoding an ERRα protein; and
(d) an agent which reduces expression of a gene encoding an ERRα protein.

In accordance with another embodiment of the present invention, a method of reducing differentiation of osteoblasts in a mammal comprises administering to the mammal an effective amount of an agent selected from the group consisting of:
(a) an ERRα antagonist;
(b) a purified antibody which binds specifically to an ERRα protein;
(c) an antisense nucleotide sequence complementary to and capable of hybridizing to a nucleotide sequence encoding an ERRα protein; and
(d) an agent which reduces expression of a gene encoding an ERRα protein.

In accordance with another embodiment of the present invention, a method for treating a disorder associated with bone loss in a mammal comprises administering to the mammal an effective amount of an agent selected from the group consisting of:
(a) an ERRα agonist;
(b) a substantially purified ERRα protein; and
(c) a nucleotide sequence encoding ERRα protein.
(d) an agent which enhances expression of a gene encoding an ERRα protein.

In accordance with another embodiment of the present invention, a method for treating a disorder associated with unwanted bone formation comprises administering to the mammal an effective amount of an agent selected from the group consisting of:
(a) an ERRα antagonist;
(b) a purified antibody which binds specifically to an ERRα protein;
(c) an antisense nucleotide sequence complementary to and capable of hybridizing to a nucleotide sequence encoding an ERRα protein; and
(d) an agent which reduces expression of a gene encoding an ERRα protein.

In accordance with another embodiment of the present invention, a method for screening a candidate compound for its ability to modulate ERRα activity comprises:
(a) providing a system for measuring a biological activity of ERRα; and
(b) measuring the biological activity of ERRα in the presence or absence of the candidate compound,
wherein a change in ERRα activity in the presence of the compound relative to ERRα activity in the absence of the compound indicates an ability to modulate ERRα activity.

In accordance with another embodiment of the present invention, a method for screening a candidate compound for potential efficacy in promoting bone formation comprises:
(a) providing an assay system for determining ERRα agonist activity of a compound; and
(b) testing the candidate compound for ERRα agonist activity in the assay wherein ERRα agonist activity in the candidate compound indicates potential efficacy as a promoter of bone formation.

In accordance with another embodiment of the present invention, a method for screening a candidate compound for potential efficacy in inhibiting bone formation comprises:
(a) providing an assay system for determining ERRα antagonist activity of a compound; and
(b) testing the candidate compound for ERRα antagonist activity in the assay wherein ERRα antagonist activity in the candidate compound indicates potential efficacy as an inhibitor of bone formation.

In accordance with another embodiment of the present invention, a pharmaceutical composition comprises an effective amount of an agent selected from the group consisting of:
(a) an ERRα agonist;
(b) a substantially purified ERRα protein; and
(c) a nucleotide sequence encoding ERRα protein and a pharmaceutically acceptable carrier.
(d) an agent which enhances expression of a gene encoding an ERRα protein.

In accordance with another embodiment of the present invention, a pharmaceutical composition comprises an effective amount of an agent selected from the group consisting of:
(a) an ERRα antagonist;
(b) a purified antibody which binds specifically to ERRα protein;
(c) an antisense nucleotide sequence complementary to and capable of hybridizing to a nucleotide sequence encoding ERRα protein; and
(d) an agent which reduces expression of the gene encoding ERRα protein and a pharmaceutically acceptable carrier.

SUMMARY OF THE DRAWINGS

Certain embodiments of the invention are described, reference being made to the accompanying drawings, wherein:

FIG. 1, Panel B shows ERRα mRNA expression normalized against that of the ribosomal protein L32; the Y-axis is the ratio of the ERRα signal to that of L32. For comparison, mRNA levels for three osteoblast markers, alkaline phosphatase (ALP), osteopontin (OPN) and osteocalcin (OCN), are also shown (Panel A) and normalized against L32 (Panel B).

DETAILED DESCRIPTION OF THE INVENTION

Figure 1:
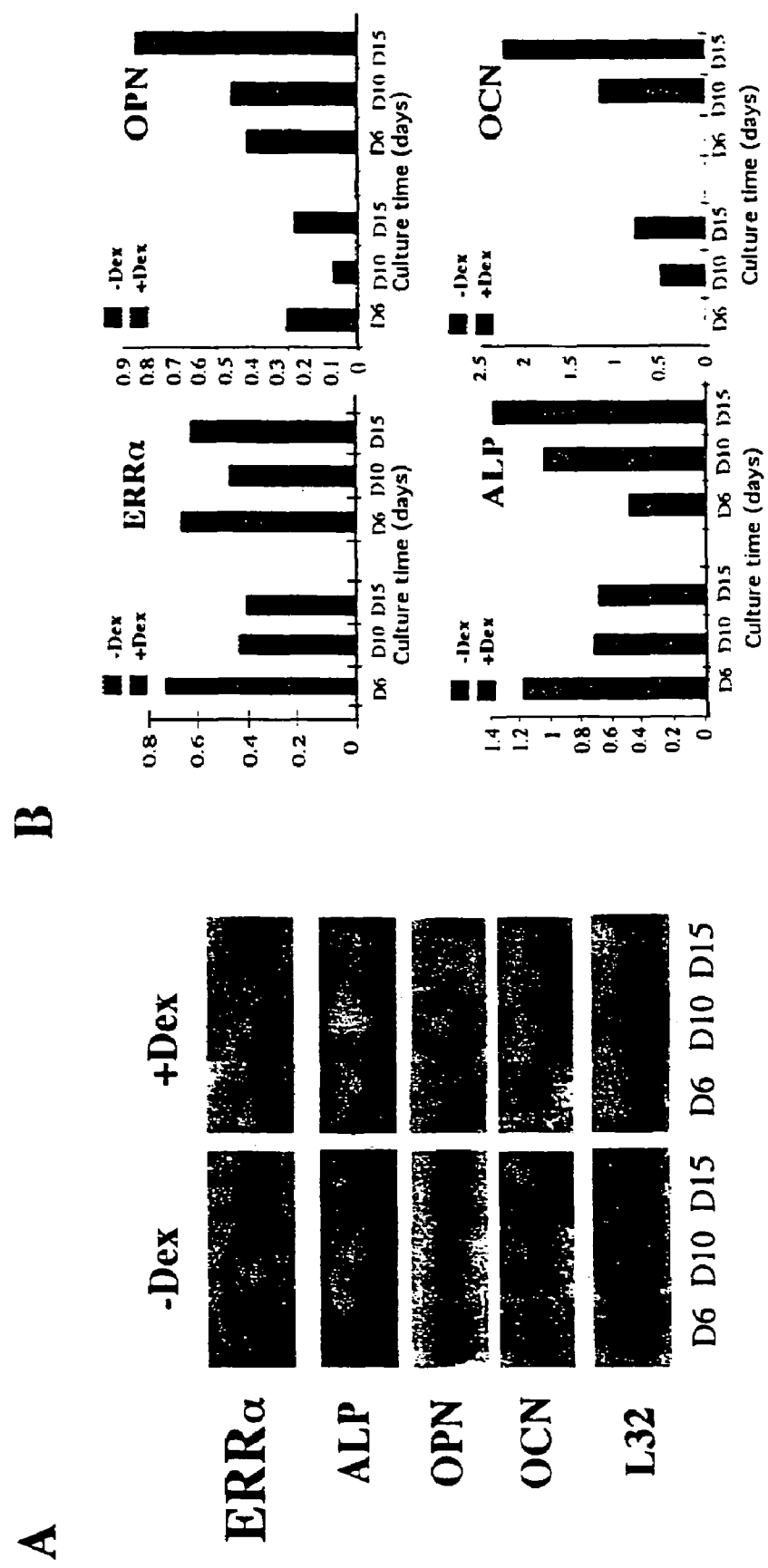
FIG. 1, Panel A is a Northern blot showing expression of ERRα, alkaline phosphatase (ALP), osteopontin (OPN) and osteocalcin (OCN), in primary rat calvaria (RC) cells over a proliferation-differentiation time course in presence (+Dex) or absence (−Dex) of dexamethasone (Dex) during proliferation (day 6), early nodule formation (day 10) and nodule mineralization (day 15).

The present invention demonstrates a new role for the orphan receptor, estrogen related receptor alpha (ERRα), namely the modulation of bone formation in mammals.

Bone formation occurs during fetal development and postnatal growth and also during adult life either at a low rate as part of normal bone remodelling or at an accelerated rate in response to injury or abnormal bone loss. Bone formation involves a number of processes, including osteoblast progenitor cell proliferation, osteoblast differentiation from progenitor cells and mineralisation of matrix produced by the osteoblasts. The inventors have shown that ERRα plays a role in all of these processes.

In a rat calvaria cell culture system, which is an accepted model of bone formation, it has been shown that upregulation of ERRα levels increased osteoblast differentiation and bone formation, while down regulation of ERRα led to inhibition of bone formation, with reduction of osteoblast numbers and differentiation, and a proliferation-independent, complete inhibition of both mineralised and unmineralised bone nodule formation.

ERRα has been shown in this system and in adult rat bone marrow stromal cell cultures, a second well-characterized system of osteoprogenitor cell proliferation and differentiation, to be expressed throughout all stages of osteoblastic differentiation. ERRα is more highly expressed in cuboidal osteoblastic cells than in surrounding non-nodular/fibroblastic cells, and nuclear expression of ERRα increased as osteoblasts matured. Immunocytochemistry showed that ERRα is also highly expressed in vivo in developing fetal rat calvaria, both in sutural cells and cells at the osteogenic front, on trabecular and remodeling bone. ERRα is also highly expressed in fetal and adult osteocytes in calvaria and in other bones including femurs.

A number of disorders are associated with bone loss or bone degeneration. Such disorders include osteoporosis, osteoarthritis, Paget's disease, periodontal disease, osteolytic bone tumour metastases in, for example, breast cancer and multiple myeloma, osteochondrodysplasias, osteogenesis imperfecta, sclerosing bone displasias and osteomalacia.

The present invention provides methods and pharmaceutical compositions for treating such disorders to promote bone formation, by increasing ERRα activity. ERRα activity may be increased in a subject either by increasing the amount of ERRα protein present or by stimulating the activity of existing ERRα protein. Increased ERRα activity may be achieved, for example, by up regulating expression of the ERRα gene, by gene therapy to provide a nucleotide sequence encoding ERRα protein, by administering an agent which enhances ERRα expression, by administering ERRα protein or by administering an ERRα agonist.

Another group of diseases involves unwanted or inappropriate bone formation. Such diseases include fibrodysplasia ossificans progressive, osteoblastic bone metastases such as prostate cancer and osteosarcomas. The present invention provides methods and pharmaceutical compositions for treating such disorders by reducing ERRα activity. ERRα activity may be reduced by reducing the amount of ERRα protein being produced or by inhibiting the activity of ERRα protein. This may be achieved, for example, by administering an antisense sequence or an agent which reduces ERRα expression, an antibody which binds specifically to ERRα protein or an ERRα antagonist.

The invention also provides a method for screening a candidate compound for its ability to modulate ERRα activity in a suitable system, in the presence or absence of the candidate compound. A change in ERRα activity in the presence of the compound relative to ERRα activity in the absence of the compound indicates that the compound modulates ERRα activity. If ERRα activity is increased relative to the control in the presence of the compound, the compound is an ERRα agonist. Conversely, if ERRα activity is decreased in the presence of the compound, the compound is an ERR antagonist.

Suitable systems for measuring ERRα activity include examination of osteoblast proliferation or osteoblast differentiation in rat calvaria cell cultures or in bone marrow stromal cell cultures as described herein or other systems known to those of ordinary skill in the art, such as organ cultures of calvaria or femur bones or injection over the calvaria in vivo.

In accordance with a further embodiment of the invention, the ERRα signalling pathway may be modulated by modulating the binding of the ERRα to an ERRα binding partner. Such a binding partner may include for example the estrogen receptor. ERRα can be used to upregulate the transcription and thus expression of genes which work together with ERRα to affect skeletal development.

The invention further provides methods for screening candidate compounds to identify those able to modulate signalling by ERRα through a pathway involving ERRα.

For example, the invention provides screening methods for compounds able to bind to ERRα which are therefore candidates for modifying the activity of ERRα. Various suitable screening methods are known to those in the art, including immobilization of ERRα on a substrate and exposure of the bound ERRα to candidate compounds, followed by elution of compounds which have bound to the ERRα.

The invention also provides a method of modulating a ERRα signaling pathway by increasing or decreasing the availability of ERRα or by modulating the function of the ERRα.

The invention further provides methods for preventing or treating diseases characterised by an abnormality in an ERRα signaling pathway which involves ERRα, by modulating signaling in the pathway.

According to another aspect of the present invention is a method for suppressing in a mammal, the proliferation of a cell capable of being stimulated to proliferate by ERRα, the method comprising administering to the mammal an effective amount of a ERRα antagonist or an antibody which binds specifically to ERRα. Such cells include but are not limited to primitive osteoprogenitor cells.

The invention also enables transgenic non-human animal models, which may be used for study of the effects of over and under expression of the ERRα gene, for the screening of candidate compounds as potential agonists or antagonists of this receptor and for the evaluation of potential therapeutic interventions.

The transgenic animals of the invention may also provide models of disease conditions associated with abnormalities of ERRα expression. Animal species suitable for use in the animal models of the invention include mice, rats, rabbits, dogs, cats, goats, sheep, pigs and non-human primates.

Animal models may be produced which over-express ERRα by inserting a nucleic acid sequence encoding ERRα into a germ line cell or a stem cell under control of suitable promoters, using conventional techniques such as oocyte microinjection or transfection or microinjection into stem cells. Animal models can also be produced by homologous recombination to create artificially mutant sequences (knock-in targeting of the ERRα gene) or loss of function mutations (knock-out targeting of the ERRα gene). For example, knock-out targeting of the ERRα gene). For example, knock-out animal models can be made using the tet-receptor system described U.S. Pat. No. 5,654,168 or the Cre-Lox system described, for example, in U.S. Pat. Nos. 4,959,717 and 5,801,030.

In accordance with one embodiment of the invention, transgenic animals are generated by the introduction of a ERRα transgene into a fertilized animal oocyte, with subsequent growth of the embryo to birth as a live animal. The ERRα transgene is a transcription unit which directs the expression of ERRα gene in eukaryotic cells. To create the transgene, ERRα gene is ligated with an eukaryotic expression module. The basic eukaryotic expression module contains a promoter element to mediate transcription of ERRα sequences and signals required for efficient for termination and polyadenylation of the transcript. Additional elements of the module may include enhancers which stimulate transcription of ERRα sequences. The most frequently utilized termination and polyadenylation signals are those derived from SV40. The choice of promoter and enhancer elements to be incorporated into the ERRα transgene is determined by the cell types in which ERRα gene is to be expressed. To achieve expression in a broad range of cells, promoter and enhancer elements derived from viruses may be utilized, such as the herpes simplex virus thymidine kinase promoter and polyoma enhancer. To achieve exclusive expression in a particular cell type, specific promoter and enhancer elements could be used, such as the promoter of the mb-1 gene and the intronic enhancer of the immunoglobulin heavy chain gene. In a preferred embodiment, a bone specific promoter such as the bone sialoprotein promoter may be used to target expression in osteoblasts.

The ERRα transgene is inserted into a plasmid vector, such as pBR322 for amplification. The entire ERRα transgene is then released from the plasmid by enzyme digestion, purified and injected into an oocyte. The oocyte is subsequently implanted into a pseudopregnant female animal. Southern blot analysis or other approaches are used to determined the genotype of the founder animals and animals generated in the subsequent backcross and intercross.

Such deficient mice will provide a model for study of the role of ERRα in bone cell differentiation and proliferation and general skeletal development. Such animals will also provide tools for screening candidate compounds for their interaction with ERRα or the signalling pathway activated by ERRα.

The invention also provides pharmaceutical compositions for promoting bone formation, comprising as active ingredient a substantially purified ERRα protein, an ERRα agonist or an isolated nucleotide sequence encoding ERRα protein.

Such compositions are useful, for example, in treating disorders associated with bone loss.

ERRα protein may be produced by conventional recombinant techniques permitting expression of ERRα by a suitable host cell. A DNA encoding ERRα may be prepared as described, for example, in Giguere et al. (1998). Techniques for production of proteins by recombinant expression are well known to those in the art and are described, for example, in Sambrook et al. (1989) or latest edition thereof. Suitable host cells include *E. coli* or other bacterial cells, yeast, fungi, insect cells or mammalian cells.

The invention provides for compositions for promoting bone formation comprising as active ingredient an ERRα agonist obtained by using a screening method as described herein.

It may be advantageous, in treating disorders associated with bone loss, to employ a combination therapy, first administering an agent such as a biphosphonate to suppress osteoclast function, followed after a suitable period of time, by administration of a pharmaceutical composition for promoting bone formation, as described herein. Such treatment regimens are well known to those of ordinary skill in the art.

A nucleotide sequence encoding ERRα protein may be administered to a subject experiencing bone loss due to an absent or defective ERRα gene either in vivo or ex vivo. Expression may be targeted to a selected cell or tissue by use of an appropriate promoter, for example the bone-specific promoter for bone sialoprotein (Stein et al. (2000)). For example, stem cells or bone marrow stromal cells may be obtained from a subject and treated in vivo with the nucleotide sequence, the cells then being restored to the subject. Such methods are described in Horwitz et al. (1999).

The invention also provides pharmaceutical compositions for reducing bone formation, comprising as active ingredient an antibody which binds specifically to ERRα, an ERRα antagonist or a negative regulator such as an antisense nucleic acid or a dominant negative mutant version of the ERRα gene.

The invention provides for compositions for reducing bone formation comprising as active ingredient an ERRα antagonist obtained by using a screening method as described herein.

Antibodies which bind specifically to ERRα protein may be made by conventional techniques.

The term "antibodies" includes polyclonal antibodies, monoclonal antibodies, single chain antibodies and fragments such as Fab fragments.

In order to prepare polyclonal antibodies, fusion proteins containing defined portions or all of an ERRα protein can be synthesized in bacteria by expression of the corresponding DNA sequences, as described above. Fusion proteins are commonly used as a source of antigen for producing antibodies. Alternatively, the protein may be isolated and purified from the recombinant expression culture and used as source of antigen. Either the entire protein or fragments thereof can be used as a source of antigen to produce antibodies.

The purified protein is mixed with Freund's adjuvant and injected into rabbits or other appropriate laboratory animals. Following booster injections at weekly intervals, the animals are then bled and the serum isolated. The serum may be used directly or purified by various methods including affinity chromatography to give polyclonal antibodies.

Monoclonal anti-ERRα antibodies may be produced by methods well known in the art. Briefly, the purified protein or fragment thereof is injected in Freund's adjuvant into mice over a suitable period of time, spleen cells are harvested and these are fused with a permanently growing myeloma partner and the resultant hybridomas are screened to identify cells producing the desired antibody. Suitable methods for antibody preparation may be found in standard texts such as Barreback, E. D. (1995).

The pharmaceutical compositions of the invention may comprise, in addition to the active ingredient, one or more pharmaceutically acceptable carriers.

Administration of an effective amount of a pharmaceutical composition of the present invention means an amount effective, at dosages and for periods of time necessary to achieve the desired result. This may also vary according to factors such as the disease state, age, sex, and weight of the subject, and the ability of the composition to elicit a desired response in the subject. Dosage regima may be adjusted to provide the optimum therapeutic response. For example, several divided doses may be administered daily or the dose may be proportionally reduced as indicated by the exigencies of the therapeutic situation.

By pharmaceutically acceptable carrier as used herein is meant one or more compatible solid or liquid delivery systems. Some examples of pharmaceutically acceptable carriers are sugars, starches, cellulose and its derivatives, powdered tragacanth, malt, gelatin, collagen, talc, stearic acids, magnesium stearate, calcium sulfate, vegetable oils, polyols, agar, alginic acids, pyrogen-free water, isotonic saline, phosphate buffer, and other suitable non-toxic substances used in pharmaceutical formulations. Other excipients such as wetting agents and lubricants, tableting agents, stabilizers, anti-oxidants and preservatives are also contemplated.

The compositions described herein can be prepared by known methods for the preparation of pharmaceutically acceptable compositions which can be administered to subjects, such that an effective quantity of the active substance is combined in a mixture with a pharmaceutically acceptable carrier. Suitable carriers and formulations adapted for particular modes of administration are described, for example, in Remington's Pharmaceutical Sciences (Remington's Pharmaceutical Sciences, Mack Publishing Company, Easton, Pa., USA 1985). On this basis the compositions include, albeit not exclusively, solutions of the substance in association with one or more pharmaceutically acceptable vehicles or diluents, and contained in buffered solutions with a suitable pH and iso-osmotic with the physiological fluids.

The pharmaceutical compositions of the invention may be administered therapeutically by various routes such as by injection or by oral, nasal, buccal,. rectal, vaginal, transdermal or ocular routes in a variety of formulations, as is known to those skilled in the art.

The present invention also enables the analysis of factors affecting the expression of the ERRα gene in humans or in animal models. The invention further provides a system for screening candidate compounds for their ability to turn on or turn off expression of the ERRα gene and the identification of binding partners which may also affect expression of ERRα or certain downstream partners.

For example, an RC cell culture system can be used to identify compounds which activate production of ERRα or, once ERRα production has been activated in the cells, they can be used to identify compounds which lead to suppression or switching off of ERRα production. Alternatively, such a cell culture system can be used to identify compounds or binding partners of ERRα which increase its expression. Compounds thus identified are useful as therapeutics in conditions where ERRα production is deficient or excessive.

The present invention enables also a screening method for compounds of therapeutic utility as antagonists of the biological activity of ERRα. Such antagonist compounds are useful, for example, to reduce or prevent differentiation and maturation of osteoblasts and osteocytes. ERRα antagonists may also be used in the treatment of bone related disorders involved inappropriate bone cell growth. Those skilled in the art will be able to devise a number of possible screening methods for screening candidate compounds for ERRα antagonism.

A screening method may also be based on binding to the ERRα receptor. Such competitive binding assays are well known to those skilled in the art. Once binding has been established for a particular compound, a biological activity assay is employed to determine agonist or antagonist potential.

ERRα is Expressed in Osteoblast Lineage Cells throughout Their Developmental Lifetime and ERRα mRNA and Protein are More Highly and Widely Expressed than either ERα and ERβ.

The inventors have shown that ERRα mRNA is expressed in differentiating primary cultures of RC cells and rat bone marrow stromal (RBM) cells and in single isolated osteoblast colonies at all detectable stages of differentiation, suggesting that ERRα may have a function in osteoblasts throughout their developmental lifetime. ERRα mRNA is present at much higher levels than either ERα or ERβ mRNA in both RC and RBM cell cultures. ERRα protein was also found more widely distributed in vitro in RC cell cultures than either ERα or ERβ. ERRα was found in most if not all cells in RC cell cultures from early proliferation stages through mineralized nodule formation. ERα was also detected in RC cells at all times analysed but at lower levels than ERRα which is also the case in rat bone marrow cultures (data not shown). ERβ, on the other hand, was more difficult to detect at any time other than in early proliferating cultures. These observations fit with the expression pattern of these three receptors in vivo in 21 day fetal calvaria. Indeed, ERRα is more highly and widely expressed than either ERα or ERβ, being highly expressed in sutural cells and all identifiable osteoblasts and osteocytes. ERα is not highly expressed in nascent, but is detectable in more mature, osteoblastic cells. ERβ, on the other hand, is more highly expressed in sutural and nascent osteoblasts. These results suggest that ERRα and ERα and/or ERβ are co-expressed in at least some osteoblastic cells, and that these receptors may act alone or together to regulate the expression of target genes in bone. It is also notable that ERRα protein is localized primarily in either the nucleus or the cytoplasm or both depending on the developmental stage of the osteoblast. This suggests that ERRα target genes and function may vary depending on the maturational stage of the osteoblastic cells.

In addition to its expression in fetal calvaria, ERRα is also highly expressed in adult calvaria and other fetal and adult bones, including long bones such as the femur. It is also throughout osteogenesis in adult rat bone marrow stromal cell cultures, suggesting that it may function throughout the lifetime of the organism and in all bones of the body irrespective of the developmental process by which they form, i.e., through an intramembranous or endochondral route. In adult quiescent bone, labeling appears highest in osteocytes, which are thought to be mechanosensors that send strain-related signals to lining cells located at the bone surface through the canicular syncytium (Huiskes et al, 2000), leading to recruitment of osteoblasts amongst other effects. These data suggest that ERRα may function not only during fetal bone development but also in adult life in both bone formation. and maintenance.

Previously, it has been shown that the estrogen receptors ERα and ERβ are themselves expressed in osteoblasts and osteocytes (Braidman et al, 1995; Onoe et al, 1997; Windahl et al, 2000), raising the possibility that ERRα and one or both of the ERs may be co-expressed in at least some osteoblastic cells. The inventors have shown by both mRNA and protein analysis that ERRα and ERα are co-distributed in large cohorts of osteoblastic cells, raising the possibility that these receptors may regulate the expression of the same target genes in bone via their known ability to participate in protein-protein interactions (Johnston et al, 1997) and their recently described capacity to bind to the same DNA target (SFRE and ERE) sequence on the osteopontin promoter (Vanacker et al, 1999).

Together, these data suggest that ERRα, ERα and perhaps ERβ are co-expressed in osteoblastic cells, and may display at least some functions in common, either singly or through their interactions, with regulatory capacities to act on target genes.

ERRα and Proliferation

Consistent with its expression in proliferating osteoblastic populations, we have found that antisense oligonucleotide-induced downregulation of ERRα inhibits proliferation of RC cell populations, an inhibition that appears to have consequences on bone nodule formation at later times (see below). The decrease in proliferation was somewhat unexpected, given our previous observation that ERRα expression appears to correlate with exit from proliferation and the onset of the differentiation process in at least certain other cell types, including the nervous system, the epidermis and muscles in the developing mouse (Bonnelye et al, 1997). This suggests that ERRα may play cell-type specific functions and is in keeping with its detection from the onset of osteogenesis in vivo (Bonnelye et al, 1997) and its presence in all osteoblastic cells including the earliest detectable osteoprogenitors (current data).

The molecular basis for the ERRα effect on proliferation is of interest. Since OPN has been described as a target gene of ERRα in in vitro promoter-reporter assays (Bonnelye et al, 1997; Vanacker et al, 1998), and since OPN is highly expressed in many proliferative populations including osteoprogenitors (FIG. 2) and in many tumour cell lines (see review in Denhardt and Noda, 1998), one candidate target in the proliferation time window for antisense-induced downregulation was OPN. However, we found no detectable downregulation of this molecule during this developmental time window, although it is clearly sensitive to regulation by ERRα later during the differentiation phase of the cultures (see below). We also found no significant changes in the antisense-treated RC populations in expression of a variety of proliferation and apoptosis/survival-associated genes expressed in osteoblasts including c-fos, Bcl-2, and Bax. However, we did observe a significant decrease in cyclin D1, a regulator of G1 phase progression. Interestingly, estrogen induces cell proliferation by stimulating progression through the G1 phase of the cell cycle (Clarke et al, 1992; Wakeling et al, 1991), and induction of cyclin Dl expression is a critical feature of the mitogenic response to estrogen. There is also a strong correlation between increased levels of cyclin D1 mRNA with estrogen receptor overexpression in breast cancer cells (Buckley et al, 1993). Recently, Sabbah et al., have described a region in the cyclin D1 promoter that confers regulation by estrogens in the human mammary carcinoma cells MCF7. The induction is strictly hormone dependant and requires the DNA binding domain as well as both AF-1 and AF-2 domains of ERα (Sabbah et al, 1999). Although no ERE has been identified in the cyclin D1 promoter, it is possible that ERα activates cyclin D1 transcription by its ability to heterodimerize with c-jun/ATF-2 (Sabbah et al, 1999). ERRα has also been described as a modulator of the estrogen receptor-mediated response of the human lactoferrin gene promoter (Yang et al., 1996), a mechanism that may also underlie its ability to regulate cyclin D1.

ERRα, Osteoblast Differentiation and Matrix Mineralization

The findings described herein show a. critical role for ERRα in bone formation, with both up- and down-regulation of bone nodule formation concomitant with up- and down-regulation of ERRα expression in vitro. Up-regulation of ERRα by transfection of RC cells with a full-length ERRα expression vector late in the proliferation time window increased bone nodule formation by an amount approximately equivalent to the transfection efficiency of the population. Concomitantly, all bone markers expressed at early differentiation stages (ALP, OPN, BSP and COLLI; Aubin and Liu, 1996) were upregulated 72 h after transfection; OCN, a late marker of the mature osteoblast, was also upregulated at days 10 and 13. Whether the increase in osteoprogenitor differentiation and bone nodule formation is a consequence of upregulation of any of these bone markers, or results from regulation of another currently unknown ERRα target gene, remains to be explicitly tested.

Figure 2:
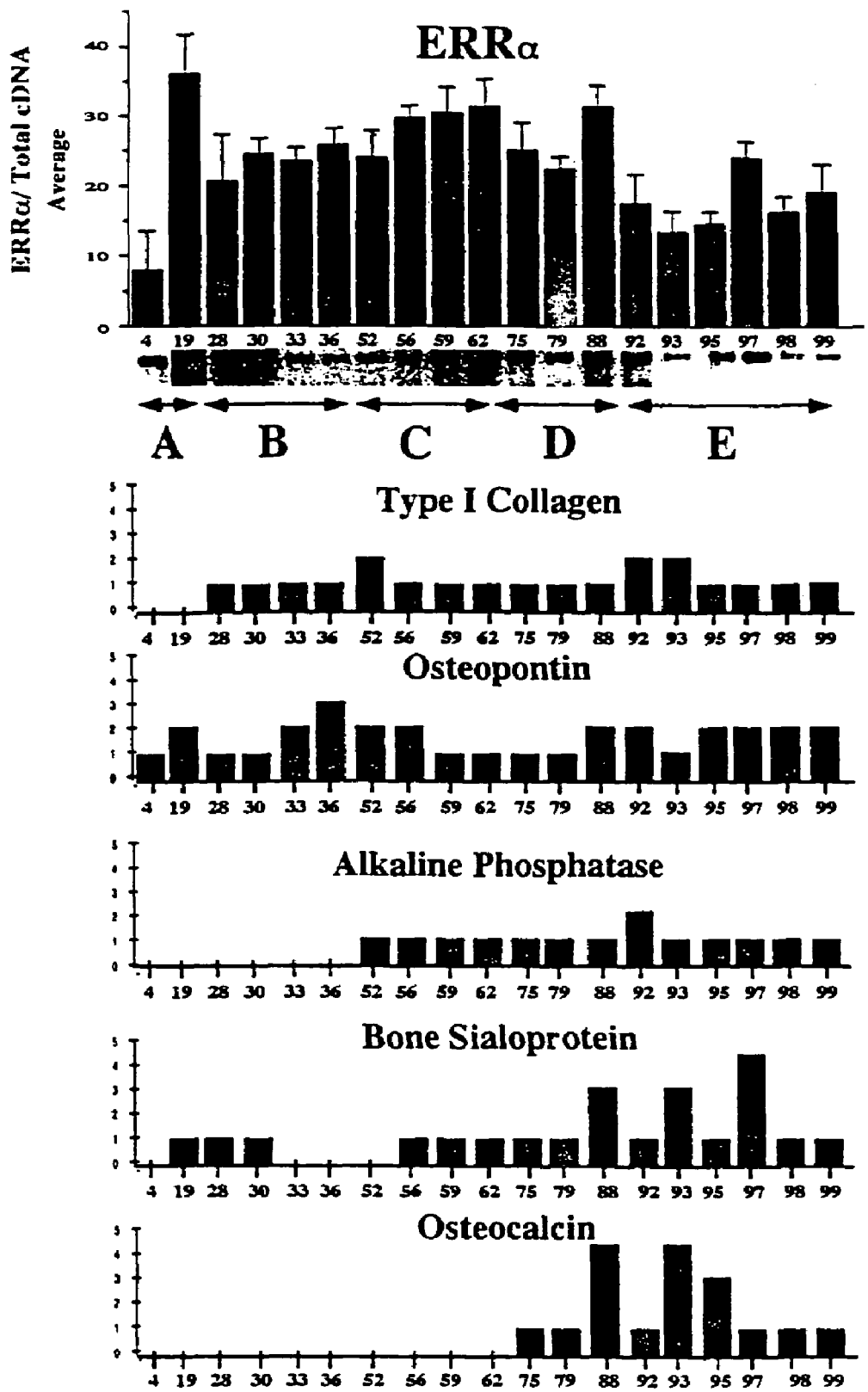
FIG. 2 shows detection of mERRα, (Type I collagen, osteopontin, alkaline phosphatase, bone sialoprotein and osteocalcin) by RT-PCR in libraries selected based on the basic molecular phenotype of the poly(A) PCR libraries made from discrete isolated colonies at different stages of osteoblast differentiation and bone development. Gene expression profiles of colonies were determined by analyzing expression of several known osteoblast lineage markers. These 19 libraries, from a pool of >100 characterized libraries, were selected for fingerprinting on the basis that they represent several transitional stages: primitive progenitors (A), progressively more mature precursors (B, C, D) and terminally differentiated, bone forming osteoblasts (E). While category order is progressive, the order of colonies within each category is random.
Figure 8:
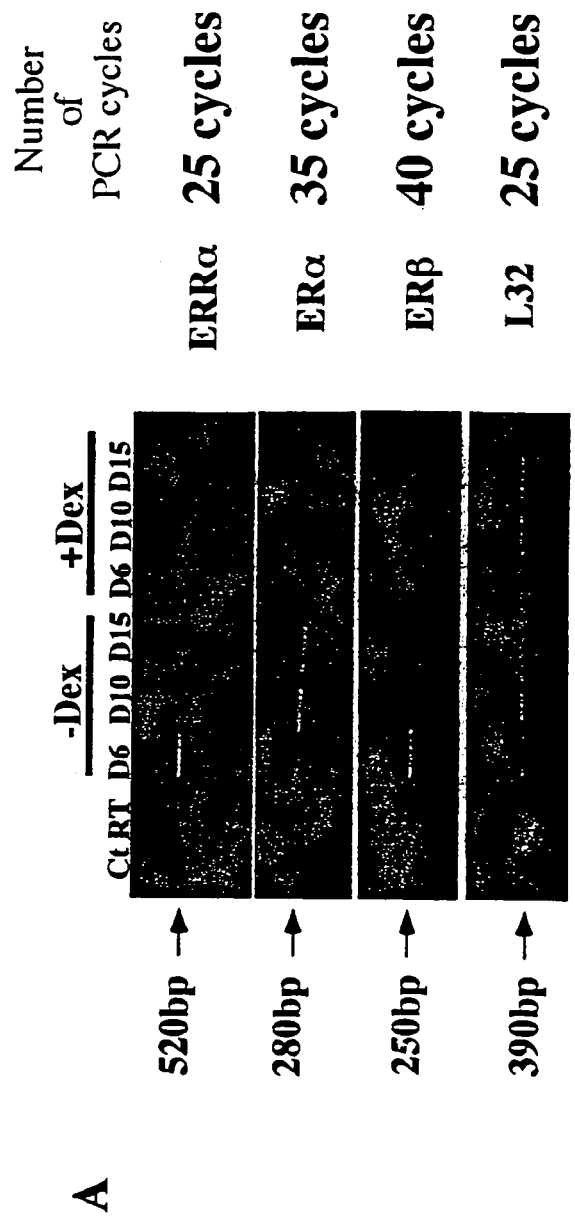
FIG. 8, Panel A shows expression of ERRα, ERα and ERβ in primary rat calvaria (RC) cells over a proliferation-differentiation time course by RT-PCR in presence (+Dex) or absence (−Dex) of dexamethasone (Dex) during proliferation (day 6), early nodule formation (day 10) and nodule mineralization (day 15). Total RNA was extracted and RT-PCR performed using specific primers for ERRα, ERα and ERβ. In Panel B, PCR product was normalized to L32 PCR product.
Figure 8:
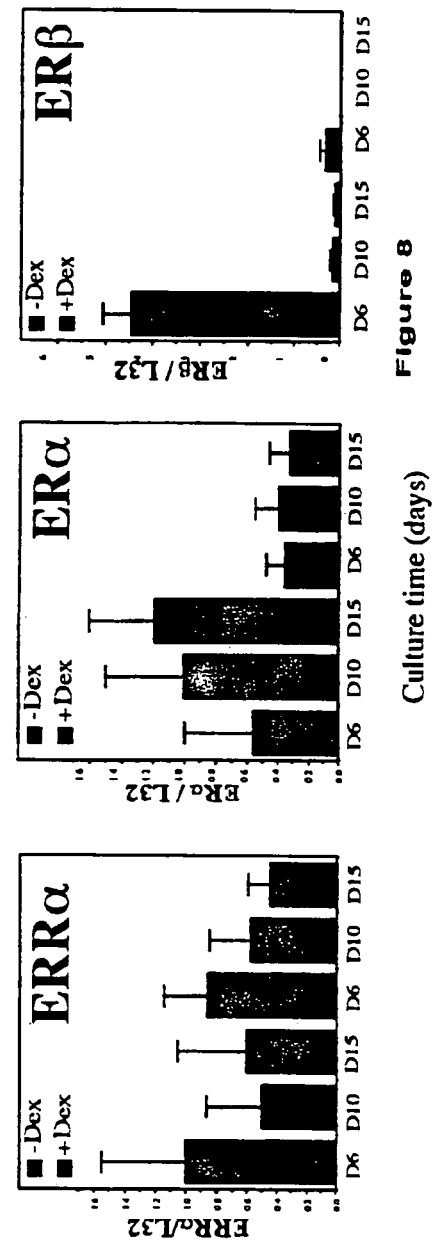

Downregulation of ERRα also had marked inhibitory effects on differentiation and bone nodule formation, when it was downregulated during proliferation phase or earlier or later in the differentiation sequence. When RC cells were treated with antisense oligonucleotides only during the proliferation window (day 1-6) and then returned to normal medium, the number of bone nodules present at day 15 was reduced compared to untreated or sense-treated cells. While one can speculate that this decrease reflects the downregulation of cyclin D1 and decreased proliferation of osteoprogenitors amongst other cells, the decrease could also reflect the concomitant downregulation of the bone "master" gene Cbfa1 (Ducy et al, 1997; Komori et al, 1997) and BSP, both of which are upregulated early during osteoprogenitor cell differentiation (Aubin and Liu, 1996; Malaval et al., 1999); we also found that BSP and ERRα are co-expressed in these very early osteoprogenitors (FIG. 2). The latter possibility is consistent with the finding that downregulation of ERRα only after proliferation has largely ceased (antisense treatment from day 5-11) results in complete inhibition of mineralized bone nodule formation, and concomitant downregulation of cbfa1, BSP and OCN. These observations, together with the data on increased bone formation when ERRα is upregulated early, suggest that at least part of the effect of ERRα on osteoblast differentiation and bone formation occurs early during the differentiation sequence, such that differentiation may not progress beyond a certain point when ERRα levels are low. In keeping with this hypothesis, large flat but ALP-positive colonies are present in antisense-treated cultures and a few cells express diminished levels of other osteoblast markers (FIG. 8).

It is also notable that ERRα also plays a role late in the differentiation/maturation sequence, i.e., when matrix is mineralizing. When RC cells were treated with antisense during late differentiation-matrix mineralization stages (day 9-15), we observed a less pronounced but nevertheless dose-dependent decrease in mineralized nodule number, but those that did form appeared to cover a larger surface area (i.e., more bone was deposited per colony) than those in control cultures.

ERRα Expression is Stimulated By Estrogen In vitro and In vivo and is Upregulated in the OVX Rat Model of Postmenopausal Osteoporosis Estrogen (17β-estradiol; E2) was found to regulate ERRα at early times in chronically treated RC cell cultures, while an acute (24 h) treatment at either day 9 or day 15 did not. These results suggest a link between ERRα and E2 in bone, most likely during the proliferation phase. Shigeta et al. showed that E2 can also activate ERRα in the uterus (Shigeta et al, 1997). Importantly, we found that 17β-estradiol also upregulates ERRα in bone in vivo. Based on the kinetics of upregulation after E2 administration, this regulation appears to be an immediate or acute response to the administration of E2. Together, these results suggest a link between ERRα and estrogens in two estrogen-sensitive tissues.

ERRα and ERα are both expressed in adult osteocytes in calvaria and long bones suggesting a function of ERRα during adult life. Bone loss in the aging skeleton is accelerated by a decrease in secretion of estrogens in post-menopausal women and can be reversed by administration of natural or synthetic estrogens. The decrease in estrogen also induces a decrease in the expression of ERα (Hoyland et al, 1999). Given these data, it was surprising to measure an increase in ERRα in OVX rats, although the acute nature of the response in vitro to estrogen supplementation, similar to the acute upregulation in vivo which was followed by downregulation, may help to explain the discrepancy. However, it is also worth noting that ERRα is highly expressed in the osteoblasts present in the high turnover bone of the OVX rats, which may indicate that ERRα expression is essential for osteoblast function in osteoporosis. The data are consistent with E2 having a biphasic effect on ERRα expression in bone.

ERRα Expression is Stimulated by TGFβ and Vitamin D3, Decreased By PTH-1-34 and Unaffected By Dexamethasone in Proliferating RC Cell Cultures ERRα is also regulated during the proliferation stages of RC cell cultures by another hormone $(1,25(OH)_2D_3)$ and a growth factor (TGFβ with potent regulatory activities in bone metabolism. Acute treatment with $1,25(OH)_2D_3$ or TGFβ for 24 hours later in the developmental sequence (at day 9 or day 15) had no effect on ERRα expression. It will therefore be of interest to determine whether $1,25(OH)_2D_3$ and TGFβ effects may be mediated at least in part by its abilities to modify ERRα levels. There was also a down regulation of ERRα by PTH-1-34 during proliferation which was most evident late in RC cultures when mineralized nodules are present. However, acute treatment with PTH-1 -34 for 24 hours at day 7 or day 16 did inhibit the expression of ERRα which suggests a more direct effect of PTH-1-34 on ERRα expression compared to E2, $1,25(OH)_2D_3$ or TGFβ.

ERRα expression in RC and RBM cell populations is almost the same in cells grown without (–Dex) or with (+Dex) dexamethasone. A 24 hour acute treatment of RC cells with Dex at day 9 or day 15 also had no effect on the ERRα expression level. These results suggest that, in RC and RBM cell populations, Dex has no effect on the expression of ERRα while it does downregulate ERα and even more potently downregulates ERα, suggest differential regulation by glucocorticoids of ERRα versus the ERs.

EXAMPLES

The examples are described for the purposes of illustration and are not intended to limit the scope of the invention.

Methods of chemistry, molecular biology, protein and peptide biochemistry and immunology referred to but not explicitly described in this disclosure and examples are reported in the scientific literature and are well known to those skilled in the art.

The following materials and methods were employed in the Examples which follow.

Cell Culture

Cells were enzymatically isolated from the calvaria of 21 d Wistar rat fetuses by sequential digestion with collagenase as described previously (Bellows, 1986). Cells obtained from the last four of the five digestion steps (populations II-V) were pooled and plated in T-75 flasks in α-MEM containing 15% heat-inactivated FBS (Flow Laboratories, McLean, Va.) and antibiotics comprising 100 mg/ml penicillin G (Sigma Chemical Co., St. Louis, Mo.), 50 mg/ml gentamycin (Sigma), and 0.3 mg/ml fungizone (Flow Laboratories). After 24 h incubation, attached cells were washed with PBS to remove nonviable cells and other debris, and then collected by trypsinization using 0.01% trypsin in citrate saline. Aliquots were counted with a Coulter Counter (Coulter Electronics, Hialeah Fla.), and the remaining cells were resuspended in the standard medium described above. The resuspended cells were plated into 100 mm tissue culture dishes at $10^5$ cells/dish, into 35 mm tissue culture dishes at $2 \times 10^4$/dish and in 24 wells plates at $10^4$ cells/well. After 24 h incubation, medium was changed and supplemented with 50 μg/ml ascorbic acid, 10 mM sodium β-glycerophosphate, and with or without $10^{-8}$ M dexamethasone (Merck, Sharp, and Dohme, Canada, Ltd., Kirkland, PQ), or $10^{-8}$ M 17β-estradiol (E2; Sigma), or $10^{-9}$ M $1,25(OH)_2D_3$, or 10 M $PGE_2$, $10^{-10}$ M TGFβ or $10^{-11}$ M 1-34 PTH (Sigma). Medium was changed every 2 days. All dishes were incubated at 37° C. in a humidified atmosphere in a 95% air/5% $CO_2$ incubator.

Bone marrow stromal cells from the femurs of young male Wistar rats, 110-120 g body weight, were cultured essentially as described (Aubin et al, 1998). The rats were killed by cervical dislocation, the femurs were dissected under aseptic conditions and placed in medium (MEM) containing antibiotics (1 mg/ml penicillin G (Sigma Chemical Co., St. Louis, Mo.), 500 μg/ml gentamycin sulfate (Sigma) and 3 μg/ml fungizone (Flow Laboratories, McLean, Va.) (designated 10X AB)). The adherent connective tissue and muscles were removed, the femurs were placed in fresh 10X AB, and their ends (epiphyses and metaphyses) were cut off with a scalpel. With a 22 gauge needle and syringe, 5 ml of MEM were flushed through each femur until the bone appeared blanched (about five to eight times). The resulting cell suspension was flushed through a syringe several times to produce a largely single cell suspension; cells recovered from two femurs were added to a T-75 tissue culture flask (Falcon) and incubated in a 37° C. humidified 95% air/5% $CO_2$ incubator. Growth medium, consisting of MEM containing 10% fetal calf serum, antibiotics (100 μg/ml penicillin G, 50 μg/ml gentamycin and 0.3 μg/ml fungizone), 50 μg/ml ascorbic acid, and $10^{-8}$ M dexamethasone (Sigma), was changed every 2-3 days. After 7 days, cells in each T-75 cell culture flask were washed with 15 ml of warm PBS and adherent cells were recovered with a mixture of 3 ml of 0.2% trypsin (w/v in citrate saline) and 2 ml of collagenase. Recovered cells were passed through a syringe with a 22 gauge needle to insure a single cell suspension. Cells were then counted on a Coulter Counter (Coulter Electronics, Hialeah Fla.) and plated at densities between $5 \times 10^3$ and $2 \times 10^4$ cells/35 mm dish and $2 \times 10^5$ cells/100 mm dish (Falcon). Cells were cultured in αMEM supplemented as above and changed every 2-3 days, for approx. 17 days until mature bone nodules were seen. To promote mineralization, 10 mmol/ml of β-glycerophosphate (Sigma) was added for at least 2 days of culture prior to fixation. Cultures were then stained and the colonies quantified as indicated in what follows.

Northern Blots

Total RNA was extracted with guanidine from RC cells at different times of the culture corresponding to different stages of proliferation, differentiation and bone nodule formation (Current Protocols in Molecular Biology, vol. 1, 1996). Northern blots were prepared and hybridized with a 750bp fragment corresponding to the rat 3' UTR of ERRα according to standard procedures (Chirgwin et al, 1979). Rat α1 COLL-I (Genovese et al.) was a 900bp cDNA PstI fragment containing the entire 3' noncoding region and one-half of the C-terminal of the propeptide of the α1 chain of type I. Rat bone/liver/kidney ALP (Noda et al., 1987) was a 600 bp cDNA EcoRI fragment obtained by digesting pRAP54 with BssHII-XhoI to remove 1.8 kb of the 5' region and religating the blunt ends. Rat OPN was a 700 bp cDNA BamHI-EcoRI fragment obtained by digesting the full length cDNA with PvuI to remove 800 bp of 5' region and ligating the blunt ended fragment into SmaI cut pGEM-7Zf(+) vector (Promega, Madison, Wis.). Rat OCN was a partial cDNA containing 350 bp of the 3' UTR isolated with OCN-specific primers from a λgt11 library prepared from ROS 17/2.8 cells, rat BSP was a partial cDNA containing 500bp of 3' region isolated with BSP-specific primers from a λgt11 library prepared from RC cells forming bone nodules, and rat L32 was generated from RC cell mRNA by PCR using specifics primers; the identities of the OCN, BSP and L32 probes were confirmed by sequencing (Liu et al., 1994).

RT-PCR

Samples of total cellular RNA (1.5-5 μg) were reverse-transcribed using oligo dT and the first strand synthesis kit of Superscript™ II, Gibco BRL. PCR was performed with specific primers specific for ERRα. Primers, located in different exons, were as follows:

| | |
|---|---|
| ERRα upstream (3'UTR): | CAG GAA AGT GAA TGC CCA GG (SEQ ID NO:1) |
| ERRα downstream (3'UTR): | CTT TGC AGC AAA TAT ACA TT (SEQ ID NO:2) |
| ERα upstream (Dom D 5'): | GAG CTG CCA ACC TTT GGC CAA GT (SEQ ID NO:3) |
| ERα downstream (Dom D 3'): | TGA ACT TGA TCG TGG AGA TTC (SEQ ID NO:4) |
| ERβ upstream (Dom D): | AAA GCC AAG AGA AAC GGT GGG CAT (SEQ ID NO:5) |
| ERβ downstream (Dom E): | GCC AAT CAT GTG CAC CAG TTC CTT (SEQ ID NO:6) |
| L32 upstream: | CAT GGC TGC CCT TCG GCC TC (SEQ ID NO:7) |
| L32 downstream: | CAT TCT CTT CGC TGC GTA GCC (SEQ ID NO:8) |

The PCR reaction mixture contained cDNA (1 μl), 1 μl dNTP mix (20 mM), 10× PCR buffer, Q solution, 25 pmol primers and 5 Units of Taq polymerase from Quiagen. PCR was done for 25 cycles (94° C. for 1 min, 55° C. for 1 min, 72° C. for 1 min and, a final elongation step of 7 min at 72° C.) for ERRα and L32; 35 cycles (94° C. for 1 min, 55° C. for 1 min, 72° C. for 1 min and a final elongation step of 7 min at 72° C.) for ERα; 45 cycles (94° C. for 1 min, 59° C. for 1 min, 72° C. for 1 min and a final elongation step of 7 min at 72° C.) for ERβ. Amplimers were sequenced for verification.

Osteoblast-associated and other markers were also amplified by PCR using specific primers for rat OCN, OPN, ALP, BSP, Cbfa1, COLL I (collagen type I α chain), C-fos, Cyclin D1, Bax and Bcl-2. PCR was done for 25 cycles (94° C. for 1 min, 55° C. for 1 min, 72° C. for 1 min and a final elongation step of 7 min at 72° C.) for OCN, OPN, ALP, BSP, L32, Bax and 30 cycles for Bcl-2, 32 cycles for c-Fos, 35 cycles for Cyclin D1 and Cbfa1 (with annealing temperatures of 58° C. and 62° C. respectively and 23 cycles for COLLI with annealing temperature of 59° C.

| | |
|---|---|
| OC upstream: | AGG ACC CTC TCT CTG CTC AC (SEQ ID NO:9) |
| OC downstream: | AAC GGT GGT GCC ATA GAT GC (SEQ ID NO:10) |
| BSP upstream: | CGC CTA CTT TTA TCC TCC TCT G (SEQ ID NO:11) |
| BSP downstream: | CTG ACC CTC GTA GCC TTC ATA G (SEQ ID NO:12) |
| ALP upstream: | CCC GCA TCC TTA AGG GCC AG (SEQ ID NO:13) |
| ALP downstream: | TAG GCG ATG TCC TTG CAG C (SEQ ID NO:14) |
| OPN upstream: | GCC ACT TGG CTG AAG CCT G (SEQ ID NO:15) |
| OPN downstream: | GAA ACT CCT GGA CTT TGA CC (SEQ ID NO:16) |
| CbfA1 upstream: | CTT CAT TCG CCT CAC AAA C (SEQ ID NO:17) |
| CbfA1 downstream: | CAC GTC GCT CAT CTT GCC GG (SEQ ID NO:18) |
| Cyclin D1 upstream: | TCC CGC CAG CAG CAA GAC AC (SEQ ID NO:19) |
| Cyclin D1 downstream: | TGA GCT TGT TCA CCA GAA GC (SEQ ID NO:20) |
| c-Fos upstream: | ATA GAG CCG GCG GAG CCG CG (SEQ ID NO:21) |
| c-Fos downstream: | AAG CCC CGG TCG ACG GGG TG (SEQ ID NO:22) |
| Bax upstream: | CCT TGG AGC AGC CGC CCC AG (SEQ ID NO:23) |
| Bax downstream: | ATG TGG GCG TCC CGA AGT AGG (SEQ ID NO:24) |
| Bcl-2 upstream: | GGG GAA ACA CCA GAA TCA AG (SEQ ID NO:25) |
| Bcl-2 downstream: | AGA GAA GTC ATC CCC AGC CC (SEQ ID NO:26) |
| COLLI upstream: | GGA GAG AGT GCC AAC TCC AG (SEQ ID NO:27) |
| COLLI downstream: | CCA CCC CAG GGA TAA AAA CT (SEQ ID NO:28) |

Poly(A) PCR Library Selection

Nineteen poly(A) PCR libraries representative of five transitional stages in osteoblast lineage progression were selected from more than one hundred available amplified colonies (Liu et al., 1994; Liu, F and Aubin, J. E., submitted). Stage A are replica-plated monolayer colonies committed to differentiate to the osteoblast lineage but not yet expressing type I αI collagen or alkaline phosphatase, both early markers of osteoprogenitor cells. Stage B and C colonies are progressively more mature, i.e. expressing type I αI collagen or both type I αI collagen and alkaline phosphatase respectively. Stage D colonies represent multilayered cells and contain histologically identifiable cuboidal osteoblasts. Stage E colonies comprised terminal differentiation stages, with multilayered cells and mineralized bone matrix. Relative amounts of total cDNA were determined by Southern hybridization and were used for normalization.

Western Blots

Total protein was extracted from confluent HeLa and MC3T3-E1cells according to standard methods (Current Protocols in Molecular Biology, vol. 1, 1996). Western blot analyses were performed using a semi-dry system. Immunoblotting was performed with rabbit polyclonal antiserum prepared against a rat peptide (NH-CPASDECEITKRR-C: SEQ ID NO:29) localized in the C domain of ERRα; blots were incubated overnight at room temperature with the antiserum diluted to 1/500, and binding was detected using HRPO-conjugated goat-anti-rabbit antibodies (1/3000; BioRad) and chemoluminescence.

Immunolabelling

Immunolabelling of cultures was done essentially as described previously (Turksen, 1991; Turksen, 1992). Cultures were rinsed with PBS, fixed with 3.7% formaldehyde in PBS and permeabilized with methanol at −20° C. Frozen sections were fixed 10 min in cold acetone. Paraffine sections were treated deparaffined in xylene, then rehydrated in 100%, 95% and 70% ethanol and water. After rinsing, cells in dishes or frozen, paraffine sections were incubated for 1 h at room temperature with 10% normal serum in PBS for ERRα and ERα and in 3% BSA in PBS (denaturated) for ERβ OCN, ALP, OPN, and BSP. After rinsing, cells or sections were incubated for 1.5 hours with appropriate dilutions of primary antibodies (1/50, anti-ERRα; anti-ERα or anti-ERβ (MC-20 or Y-19, respectively; Santa Cruz Biotechnology, Inc))(Shim et al, 1999; Saji et al, 2000; Tremblay et al 1999). The anti-rat OCN antiserum was kindly provided by Dominique Modrowski (INSERM U349, Hopital Lariboisiere, Paris, France) and used at 1/100 dilution. The anti-OPN MPIIIB10) and anti-BSP (WWVIDI) antibodies were purchased from the Hybridoma Bank (Iowa City, Iowa) and used at a 1/800 and 1/500 dilution respectively. The production and characterization of monoclonal antibody RBM 211.13 directed to rat bone/liver/kidney ALP, have been described elsewhere (Turksen and Aubin, 1991; Turksen et al., 1992); it was used at a 1/100 dilution of purified ascites fluid. 10% normal serum in PBS or 3% BSA in PBS were used as negative controls. Nodules or calvaria sections were rinsed in PBS and incubated for 1 h at room temperature with secondary antibody CY-3-conjugated anti-rabbit (Jackson Immunoresearch Lab, West Grove, Pa., USA; 1/300 final dilution) for ERRα, OC and ALP or secondary antibody anti-mouse (Jackson Immunoresearch Lab, West-Grove, Pa., USA; 1/300 final dilution) for BSP and OPN. After rinsing, samples were mounted in Moviol (Hoechst Ltd, Montreal, PQ, Canada) and observed by epifluorescence microscopy on a Zeiss Photomicroscope III (Zeiss, Oberkochen, Germany). For photography and printing, equal exposure times were used for specifically-labelled and control cultures.

Nodule Quantification

For quantification of nodule formation, dishes or wells were fixed and stained by the Von Kossa technique and bone nodules were counted on a grid (Bellows et al., 1986; Bellows and Aubin, 1989). Results are plotted as the mean number of nodules±SD of three wells for controls and each concentration of antisense or sense primers and five dishes for pcDNA3 control and pcDNA3-ERRα.

Cell Counting

For cell growth analysis, the cell layers were rinsed in PBS, released with trypsin and collagenase (1:1, vol/vol, of solutions described above), and the harvested cells were counted electronically. Results are plotted as the average of three counts for each of three dishes for control and pcDNA3-ERRα or three wells for each concentration of antisense or sense primers used.

Alkaline Phosphatase Histochemistry

The histochemical stain for alkaline phosphatase is a modification of Pearse's (1960). Cells were rinsed once with cold PBS and fixed in 10% cold neutral buffered formalin for 15 min, rinsed with distilled water, and left in distilled water for 15 min. Fresh substrate (10 mg Naphthol AS MX-PO4 (Sigma) dissolved in 400 μl N,N-dimethylformamide, then added to 50 ml distilled water and 50 ml Tris-HCl (0.2 M, pH 8.3) and then 60 mg Red Violet LB salt (Sigma)), was filtered through Whatman's No. 1 filter directly onto the dishes, and incubated for 45 min at 20° C. The dishes were then rinsed in tap water, drained and stained with 2.5% silver nitrate for 30 min at room temperature (von Kossa stain), then rinsed 3 times with tap water. The dishes were finally air dried.

Transient Transfections

Primary RC cells were grown in 35 mm tissue culture dishes at $2 \; 10^4$/dish in α-MEM containing 10% heat-inactivated FBS (Flow Laboratories, McLean, Va.) and supplemented with 50 μg/ml ascorbic acid, 10 mM sodium β-glycerophosphate, and $10^{-8}$ M dexamethasone. Cells were transfected at 50% of confluence according to the Effecten transfection protocol (Quiagen) using a pcDNA3 empty plasmid as a control and pcDNA3-ERRα (in the EcoRI cloning site) at 0.5 μg of total DNA per transfection. As control of transfection efficiency, we used a CMV-βGal vector. Nodules were counted at day 15. mRNA was extracted at 72 h, day 10 (beginning of nodules formation) and day 15 (mineralized nodules), after transfection.

Antisense and Sense Oligonucleotide Treatment

The resuspended RC cells were plated in 24 wells plates at $10^4$ cells/well. Antisense oligonucleotide inhibition of ERRα expression was accomplished with a 20-base phosphorotbioate-modified oligonucleotide, localized to the A/B domain. The ERRα antisense oligonucleatide sequence was: 5'TCAC-CGGGGGTTCAGTCTCA-3'(SEQ ID NO:30). Control dishes were treated with the complementary sense oligonucleotide or no oligonucleotide. Preliminary experiments were done to determine effective oligonucleotide concentrations that were not toxic. 0.1 μM to 5 μM oligonucleoddes were added directly to cells either during the proliferation phase (days 1 to 6) and 0.5 μM to 2 μM oligonucleotides were added during the differentiation phase (day 5 (end of proliferation) to 11) or (day 9 (nascent nodule formation) to 15) in standard medium as above supplemented with 50 μg/ml ascorbic acid, 10 mM sodium β-glyceropbosphate, and $10^{-8}$ M dexamethasone. Medium was changed every 2 days and fresh oligonucleotides were added. mRNA was collected at day 6 for the proliferation experiments and at day 15 for the differentiation experiments. Nodules were counted at 15 days.

Ovariectomized Rats and Estrogen-treated Mice 8 week-old female CBA-1 mice from the University of Bristol breeding colony were treated once weekly by subcutaneous injection with either vehicle (0.2 ml corn oil; Sigma Chemical, Poole, Dorset, U.K.) or 500 μg of 17β-estradiol (Sigma) as described (Samuels et al, 1999). This dose was chosen because it has previously been reported to cause maximal stimulation of endosteal bone formation in female mice (Brain et al, 1993). Throughout the experiment, animals received a standard diet (rat and mouse standard diet, B&K Ltd., Humbside, U.K.) and water ad libitum, and were kept with a cycle of 12 h light and 12 h darkness. Animals were sacrificed 4, 8, 12 and 24 days after the first subcutaneous injection, the tibia were removed for processing, and mRNA was extracted (Samuel and Tobias, 1999).

35-40 day old (100-125 g) Wistar rats (Charles River Breeding Laboratories, Quebec), either ovariectomized (OVX) or sham-operated (SHAM), were kept under standard diet and laboratory conditions for 4 weeks post-operation. Animals were killed, the uteri were dissected and weighed, and the femurs were removed, fixed in 4% paraformaldehyde, decalcified for 2 weeks in EDTA and processed overnight for paraffin embedding.

Example 1

ERRα mRNA and Protein are Expressed throughout All Osteoblast Proliferation and Differentiation Stages In Vitro ERRα mRNA expression levels were assessed over a proliferation-differentiation time course by Northern blotting of primary rat calvaria (RC) cell populations grown in the presence (+Dex) or absence (−Dex) of dexamethasone (Dex), a stimulator of differentiation in this model. Under both growth conditions, ERRα mRNA was expressed at all times assessed, including proliferation (day 6), early nodule formation (day 10) and nodule mineralization (day 15) (FIG. 1A, B). For comparison, mRNA levels for three osteoblast markers, alkaline phosphatase (ALP; a relatively early marker of osteoblast development), osteopontin (OPN) and osteocalcin (OCN; a late marker of osteoblast maturation), are also shown (FIG. 1 A, B).

Because RC cell cultures comprise a heterogeneous mixture of cell types and osteoblasts at different differentiation stages, we sought next to confirm that ERRα is expressed by osteoblast lineage cells. To do this, we used globally-amplified (poly(A) PCR) cDNA pools prepared previously from single isolated osteoblast colonies at different stages of differentiation (Liu et al., 1994; Liu and Aubin, submitted). Colonies used were selected based on their molecular phenotypes (relative expression levels of collagen type I (COLL I), OPN, bone sialoprotein (BSP), ALP and OCN). ERRα was amplified in each cDNA pool with specific primers for sequences in the 3' UTR of ERRA and found to be expressed at all developmental times. Notably, however, levels were generally lower in more primitive progenitors (A) and osteoblastic cells associated with mineralized nodules (E), and higher in more mature precursors (B), preosteoblasts (C) and osteoblasts (D) (FIG. 2).

Immunocytochemistry was performed to determine whether ERRα protein is expressed in RC cell cultures. A Western blot of HeLa cell extracts was used to confirm the specificity of the ERRα antiserum. A single immunoreactive band was detected at 53 Kd (FIG. 3A). In extracts of the control osteoblastic cell line, MC3T3-E1, ERRα was almost undetectable, however, a strong and single band at 53 kd was observed in cell extracts of the same line transfected with an ERRα expression vector (FIG. 3B).

Figure 3:
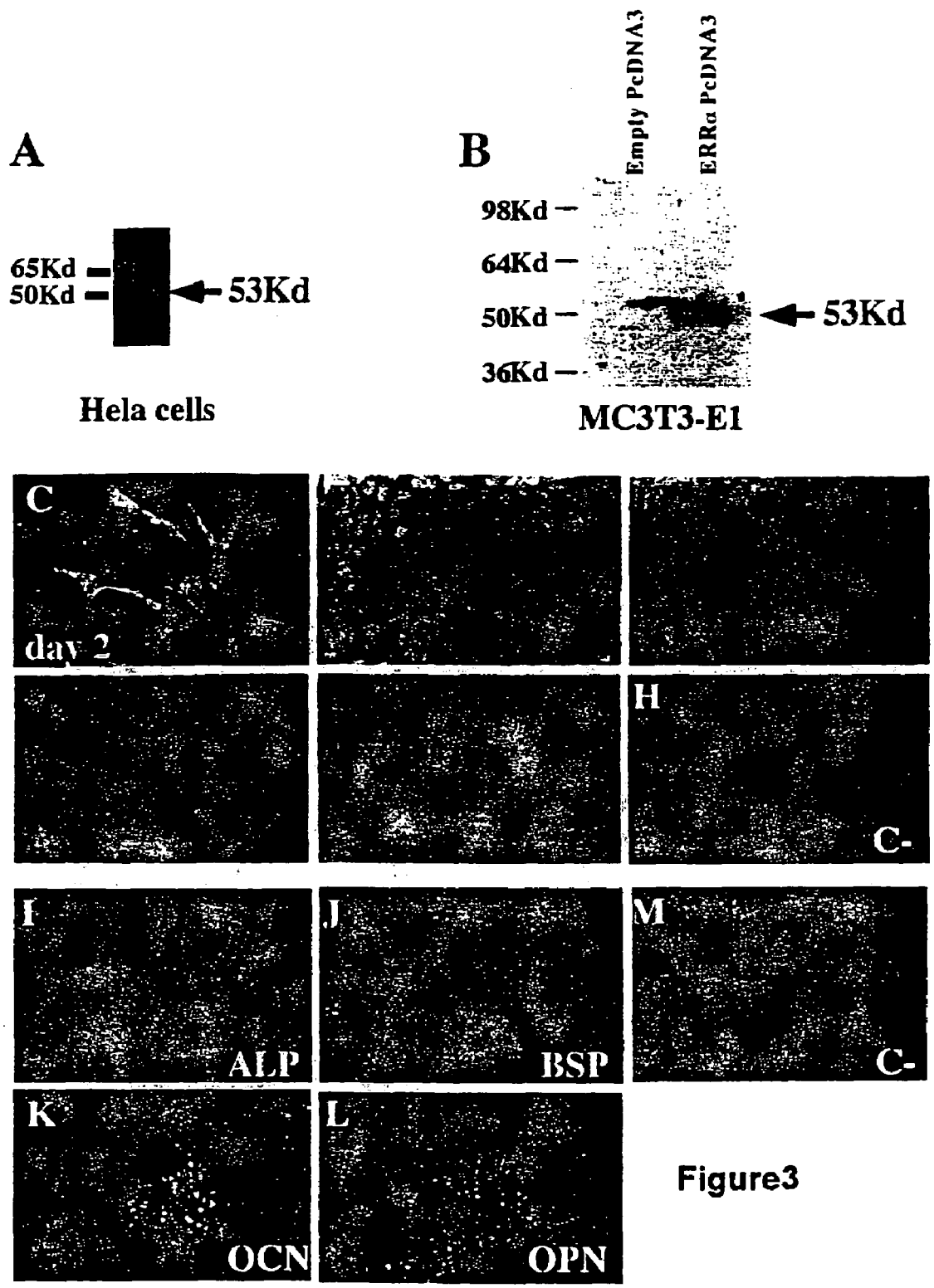
FIG. 3 shows in Panel A: a Western blot of whole-cell extracts obtained from Hela cells and, in Panel B: MC3T3-E1 transfected with the empty expression vector PcDNA3 and PcDNA3m ERRα, separated by SDS-PAGE (10% polyacrylamide). Panels C to M show immunolabelling for ERRα in RC cells over a proliferation-differentiation time course: during proliferation at day 2 (C), confluence (D), nascent nodules (E), mineralized nodules (F), osteoblasts (G). Negative control for anti-rabbit antibody is shown in (H). Immunolabelling for alkaline phosphatase ALP (I), bone sialoprotein BSP (J), osteocalcin OCN (K) and osteopontin OPN (L), are also shown. Negative control for anti-mouse antibody is shown (M).

ERRα protein was found widely distributed in most, if not all, cells in RC cell cultures at all times analysed, including early proliferation stages (FIG. 3C), confluence (FIG. 3D), when nascent nodules were forming (FIG. 3E) and when nodules were mineralizing (FIG. 3F, G). Note especially, however, that staining for ERRα was more intense in the osteoblasts associated with both early and late bone nodules than in the surrounding fibroblastic cells (FIG. 3E, F). Interestingly, while ERRα is primarily found in the cytoplasm and perinuclear location at days 2 (FIG. 3C) and 4 (data not shown), by day 6 and thereafter, including in mature osteoblasts, nuclear label is prominent (FIG. 3 E-G).

For comparison, protein expression of four osteoblast markers, ALP (FIG. 3I), BSP (FIG. 3J), OCN (FIG. 3K) and OPN (FIG. 3L), is also shown. As predicted, ERRα is co-expressed in osteoblasts with OPN, which was described earlier as a target gene of ERRα by cotransfection studies (Bonnelye et al 1997; Vanacker et al, 1998), supporting the hypothesis that ERRα may regulate OPN in osteoblasts in vivo as well. Clearly, ERRα is also highly co-expressed in cells with ALP, OCN and BSP.

Example 2

Figure 4:
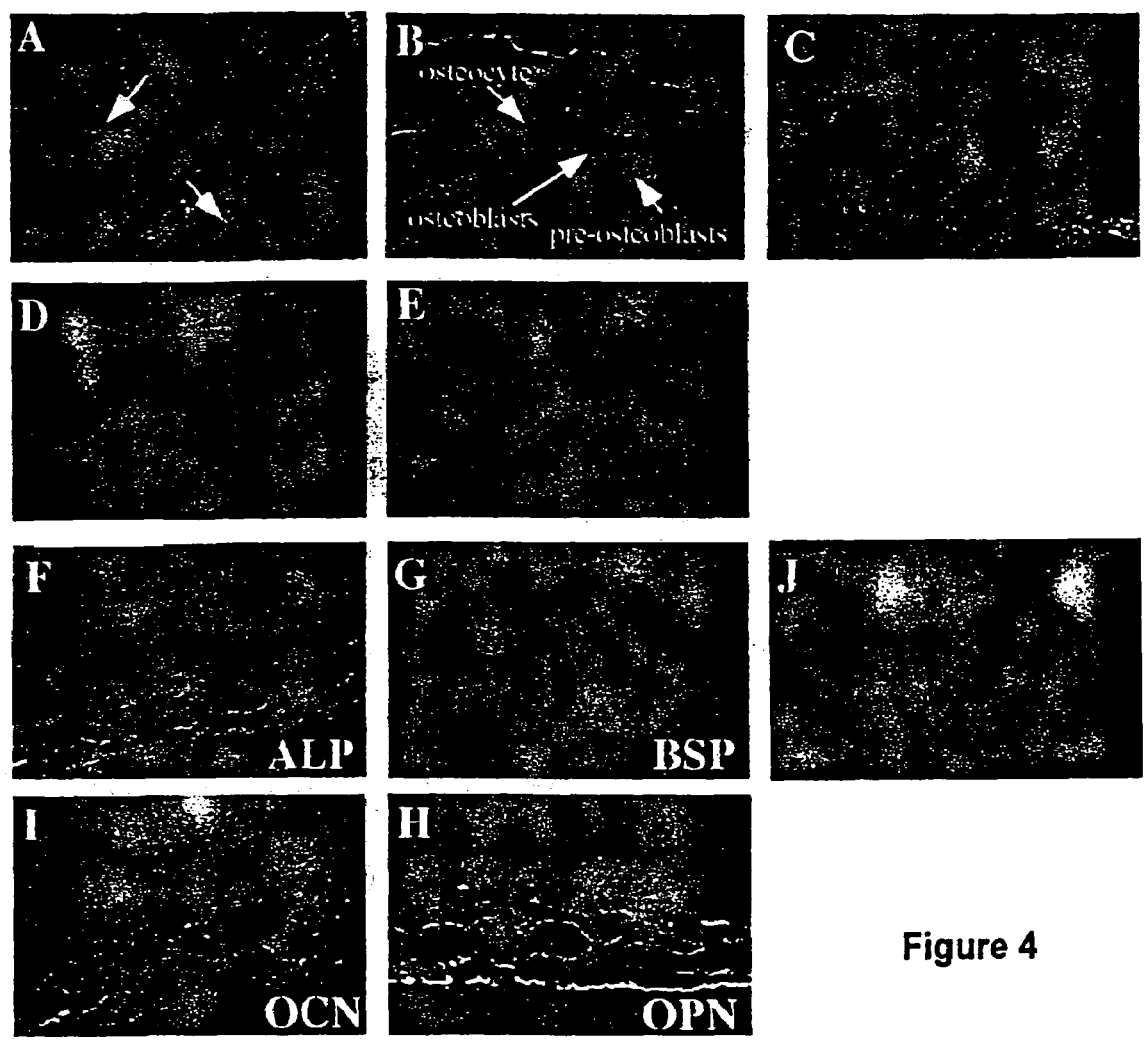
FIG. 4, Panels A to C, show photographs of 21 days fetal calvaria sections immunolabelled for ERRα. ERRα detection is seen in osteogenic front (A), more mature growing bone trabecula (B) and remodeling bone (C). Panel D shows immunolabelling for ERRα in adult calvaria, osteocytes (D). Panels F to I show immunolabelling for alkaline phosphatase ALP (F), bone sialoprotein BSP (G), osteocalcin OCN (I) and osteopontin OPN (H). Negative controls for anti-rabbit antibody and anti-mouse antibody are shown (E, J respectively).

ERRα is also Expressed in Osteoblastic Cells In Vivo in Fetal and Postnatal Rat Calvaria To extend the observations made in vitro to bones in vivo, immunocytochemistry was performed on sections of 21 d. fetal rat calvaria, the same bones used for preparation of cell cultures. Consistent with the in vitro results, ERRα was found in all detectable cohorts of osteoblasts from those associated with nascent bone at the osteogenic front (FIG. 4A) to those in the more mature growing bone trabecula (FIG. 4B) and remodeling bone (FIG. 4C). Consistent with the RT-PCR results on single bone nodules (cf. FIG. 2), ERRα was also detectable in sutural cells (arrows, FIG. 4A), preosteoblasts, osteoblasts (FIG. 4B, C) and osteocytes (FIG. 4B). ERRα was also high in the osteocytes present in postnatal (4 week) rat calvaria, suggesting that ERRα may be involved not only in the formation but also in the maintenance of bone. Also consistent with the in vitro cell labeling, ERRα in fetal calvaria in vivo is co-expressed in cells with ALP, OPN (FIG. 4F, H), BSP (FIG. 4G) and OCN (FIG. 4I).

Example 3

Inhibition of ERRα Expression Blocks the Proliferation of RC Cells and Their Differentiation to Mature Bone-forming Osteoblasts Antisense oligonucleotides form DNA:RNA duplexes with specific mRNA species, thereby blocking binding of the mRNA to the 40S ribosomal subunit and preventing translation (Reddy et al., 1994). Preliminary experiments were done to determine effective oligonucleotide concentrations that were not toxic (not shown) and the specificity of the antisense was also confirmed by immunocytochemistry on bone nodules. After 24 h of treatment or not with sense or antisense oligonucleotides, ERRα was detectable in bone nodules in untreated cultures and those treated with 1 μM sense oligonucleotides but was almost undetectable in bone nodules present in cultures treated with 1 μM antisense (data not shown).

To dissect the possible involvement of ERRα in osteoblast differentiation and bone formation, RC cells were treated at different developmental times from early proliferation stages until mineralized nodule formation.

Figure 5:
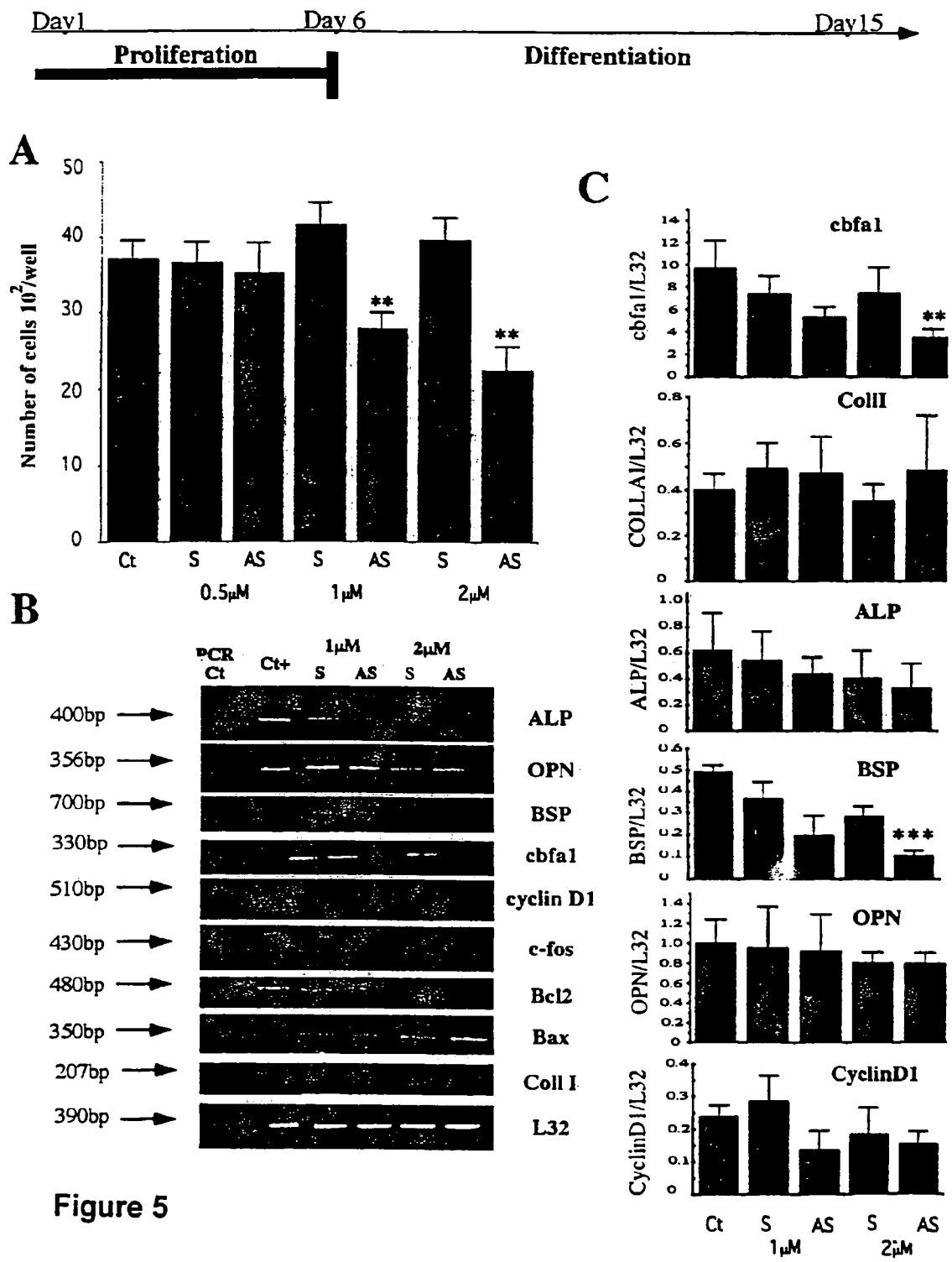
FIG. 5, panel A shows proliferation of RC cells treated with antisense/sense oligonucleotide at 0.5 µM, 1 µM and 2 µM (AS or S) or no oligonucleotide (Ct) during the proliferation stage between days 1-6. Inhibition of ERRα protein synthesis inhibited the cell proliferation based on the cell number. Three 24 wells per treatment group were trypsinized and cells were counted. Data are expressed as the cell number mean ±SEM and are representative of three independent experiment. ANOVA revealed a very highly significant (p<0.0001) effect of antisense on cell proliferation. Panel B shows expression of markers of osteoblast differentiation. Total RNA was extracted and RT-PCR performed on triplicate samples using specific primers for early markers (ALP, BSP, OPN, cbfa1, COLL I), proliferation (Cyclin D1, c-Fos) and apoptosis (Bcl2, Bax) at day 6. Panel C shows PCR product normalized to L32 PCR product. ANOVA revealed a significant (p<0.05) and a highly significant (p<0.001) effect of antisense treatment for Cbfa1 and BSP respectively. =p<0.01, *=p<0.001 vs control (Student's unpaired t-test).
Figure 6:
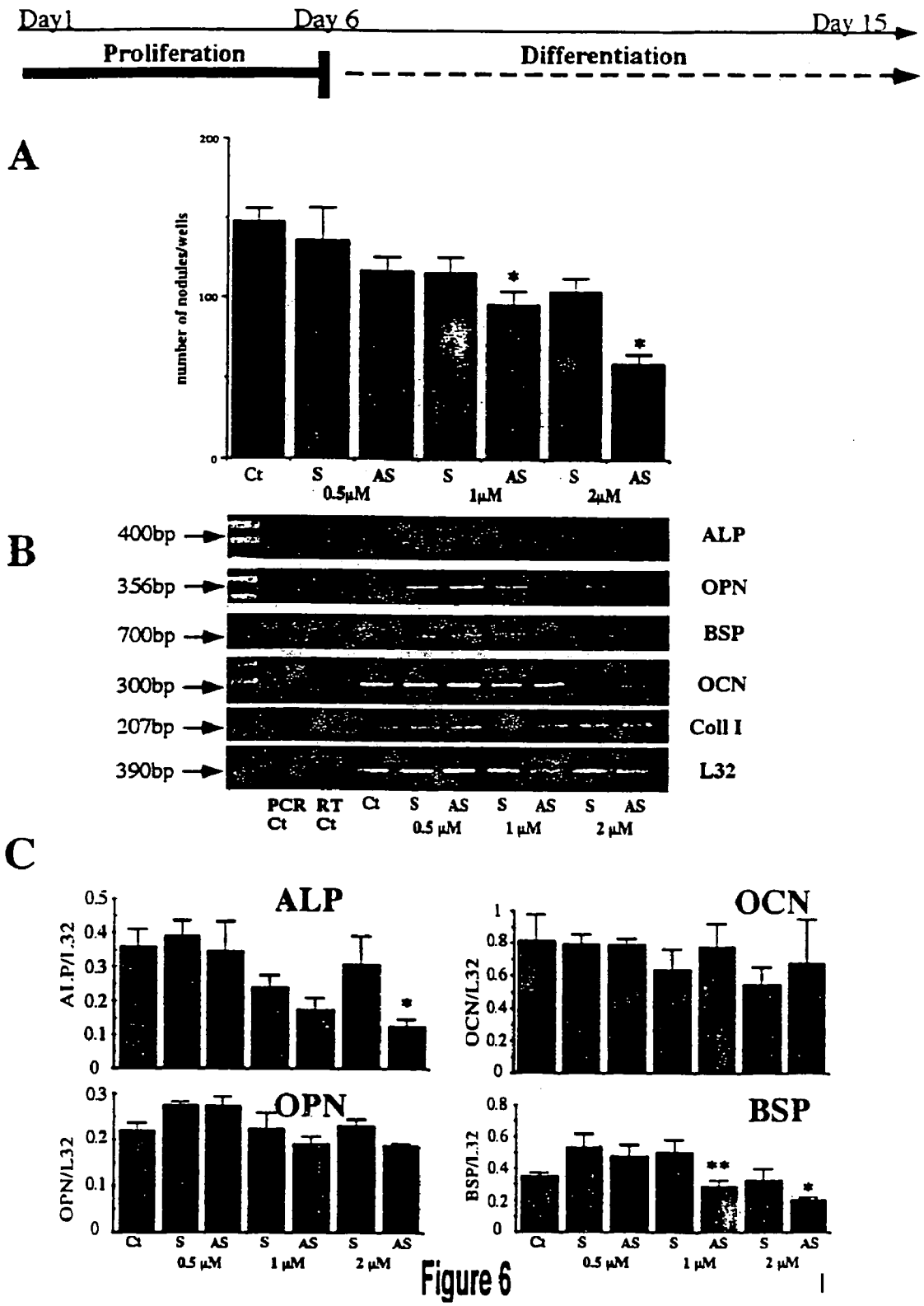
FIG. 6, Panel A shows nodule formation in RC cells treated with antisense/sense oligonucleotide at 0.5 µM, 1 µM and 2 µM or no oligonucleotide (Ct) during the proliferation stage between days 1-6 and then switched to normal differentiation medium. Inhibition of ERRα protein synthesis induced a decrease in bone nodules formation Three 24 wells per treatment group were von Kossa stained and the nodules were counted. Data are expressed as the nodule mean +/−SEM and are representative of two independent experiment. ANOVA revealed a very highly significant (p<0.0008) effect of antisense, on bone nodules formation. Panel B shows expression of osteoblast markers. Total RNA was extracted and RT-PCR performed on triplicate samples using specific primers for markers of osteoblast ALP, BSP, OPN, OCN, COLLI at day 15. Panel C shows PCR product normalized to L32 PCR product (C). ANOVA revealed a highly significant (p<0.001) effect of antisense treatment for ALP and BSP respectively. *=p<0.05, **=p<0.01, vs control (Student's unpaired t-test).

When RC cells were treated between days 1-6, the proliferation stage, a significant and specific dose-dependent decrease in cell number (30% at 1 μM and 40% at 2 μM), was found at day 6 in dishes treated with antisense compared to sense or untreated controls (FIG. 5A). These results suggest that ERRα may play a role in the proliferation or very early differentiation phases of RC cells. To analyze the underlying mechanism of ERRα action during the proliferation phase, expression of early markers of osteoblast differentiation (ALP, BSP, OPN, cbfa1, COLLI), proliferation (Cyclin D1, c-Fos) and apoptosis (Bcl2, Bax) were assessed at day 6 (FIG. 5B). BSP and cbfa1 were reduced significantly (FIG. 5C, D); Cyclin D1 was also reduced but it did not reach statistical significance. On the other hand, ALP, OPN, COLLI, c-Fos, Bax and Bcl2 were not significantly affected (FIG. 5C, D and data not shown). To determine if treatment during the proliferation time window caused a sustained alteration in differentiation, terminal differentiation/bone nodule formation was assessed at day 15 in cultures treated between days 1-6 with antisense and then switched to normal differentiation medium. A significant decrease in mineralized bone nodule number, i.e., 29% at 1 μM and 45% at 2 μM antisense oligonucleotides (FIG. 6A), was seen. Concomitantly, ALP and BSP expression remained lower than levels seen in control or sense-treated cultures, while OPN, OCN and COLLI were not significantly altered (FIG. 6B, C).

To determine whether ERRα also plays a role in osteoblast differentiation independently of an effect on proliferation, RC cells were treated with the antisense oligonucleotide beginning at day 5 (after cells had reached confluence and proliferation was decreased) to day 11. Although cell number was decreased slightly by day 15 (19% at 1 μM and 35% at 2 μM) in antisense-treated cultures, a striking dose-dependent decrease in mineralized bone nodule formation was seen, i.e., 30% at 0.5 μM, 60% at 1 μM and 100% decrease at 2 μM; the sense oligonucleotides had a small non-specific non-dose-dependent effect on nodule numbers. A similar inhibition of bone nodule formation was also observed when the osteoblastic cell line MC3T3-E1 was treated with the antisense oligonucleotides over the comparable time period. In antisense-treated cultures, ALP-positive colonies were present and large in diameter but flat, suggesting that inhibition of ERRα blocked differentiation at an early stage such that progression to matrix deposition and maturation was reduced. Consistent with this interpretation, Cbfa1, BSP and OCN were all decreased in antisense-treated cultures whereas OPN, COLLI and ALP were not affected. Immunocytochemistry confirmed the decrease in OCN- and BSP-expressing cells, but the maintenance of ALP expression in incipient bone nodules (data not shown).

To determine whether ERRα also plays a role at later stages, RC cells were treated between days 9-15, when differentiation is well-progressed and nascent nodules are becoming three-dimensional. At this stage also, while sense oligonucleotides had a small non-specific, non-dose dependent effect on nodule number, antisense oligonucleotides caused a small but nevertheless dose-dependent and significant decrease in the number of mineralized bone nodules formed, i.e., 17% at 1 μM and 27% at 2 μM. In parallel, OCN and OPN but not BSP, COLLI or ALP were decreased. Interestingly, those bone nodules that did form in antisense-treated cultures appeared to cover a greater surface area compared to those in control cultures (data not shown).

Example 4

Figure 7:
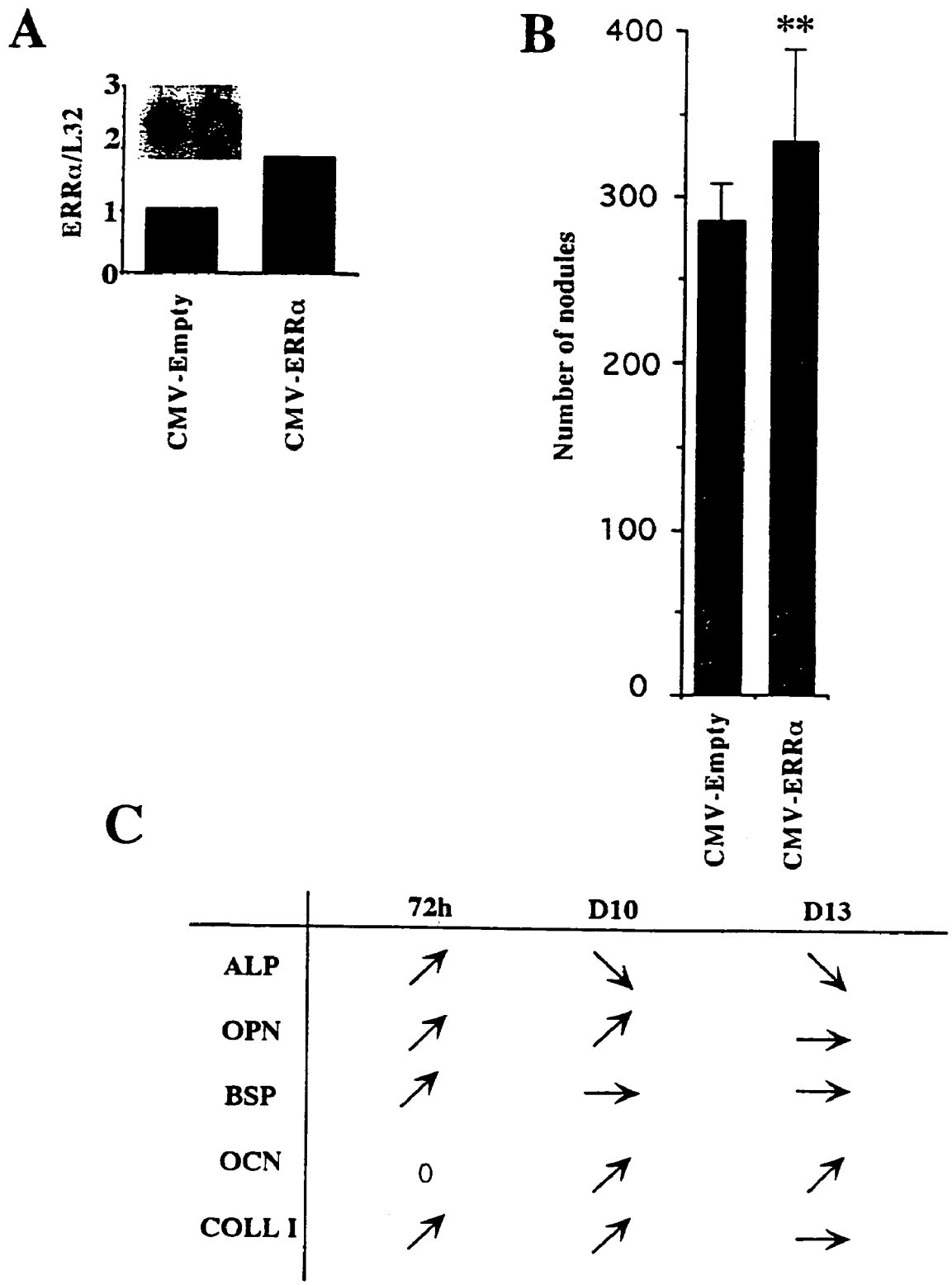
FIG. 7, Panel A shows a Northern blot of primary RC cells transfected at 50% of confluence using a pcDNA3 empty plasmid as a control and pcDNA3-ERRα at 0.5 µg of total DNA per transfection. As control, of efficiency of the transfection, total RNA of each group was extracted 72 h after transfection and northern blot was performed with samples (pool from three 35-mm culture). Panel B shows nodule numbers in five 35-mm dishes per treatment group for three independent experiments, von Kossa stained and the nodules counted. ANOVA revealed a significant (p<0.01) effect of overexpression of ERRA, on bone nodules formation. Panel C shows expression pattern, using specific probes for markers of osteoblast ALP, BSP, OPN, OCN, COLLI total RNA was extracted at 72 h after transfection, day 10 and day 13, and northern were performed (pool from three 35-mm culture). Data were pooled from three independent experiments and the pattern of expression are presented.

Overexpression of ERRα Increases Differentiation and Bone Nodule Formation in RC Cells ERRα expression was upregulated by transient transfection of RC cells at day 5 when cells were between 50-60% confluent. By using a CMV-βGal control vector, it was estimated that a maximal efficiency of transfection of 10-15% was obtained, which resulted in a 30% increase in ERRα levels observed on a Northern blot (FIG. 7A). At day 15, a significant increase (15%) in number of mineralized bone nodules was observed (FIG. 7B). In parallel, we assessed expression levels of osteoblast markers (ALP, OPN, BSP, COLLI, OCN) 72 h after transfection, at day 10 when bone nodules had started to form and at day 15 when nodules are formed and mineralized. An increase in OPN was observed at 72 h and d 10 in cultures overexpressing ERRα, consistent with previous data describing OPN as a target gene of ERRα in reporter assays (Bonnelye et al, 1997a, Vanacker et al, 1998) (FIG. 7C). COLL I was also increased at the early time points, suggesting a role for ERRα in the formation of a major component of the bone extracellular matrix. OCN, a mature osteoblast marker expressed only at later differentiation times, was undetectable at 72 h, but was increased at both day 10 and 15, whereas BSP was increased 72 h after transfection but not detectably altered at later times. Finally, ALP, which was increased 72 h after transfection, was lower at days 10 and 15 (FIG. 7C).

Example 5

ERRα mRNA is More Highly Expressed in RC Cell Cultures than either ERα and ERA mRNA and Expression Patterns Vary The expression of ERRα mRNA in RC cultures and single bone nodules prompted a comparison of the levels of its expression with those of the two estrogen receptors, ERα and ERA When RT-PCR was done with primers specific for each of these three receptors, ERRα was found to be expressed at significantly higher levels than either ERα and ERβ and the two estrogen receptors were themselves present at different levels (i.e., ERRα was easily detected at 25 cycles, while 35 cycles and 40 cycles were required to detect ERα and ERβ respectively). In addition, the expression patterns of the three receptors over the proliferation-differentiation time course in RC cell cultures was strikingly different. Similarly to ERRα, which decreased slightly, ERA decreased markedly over time in −Dex cultures, whereas ERα increased (FIG. 8A, B). On the other hand, both ERRα and ERβ decreased over time in +Dex cultures, but ERα did not (FIG. 8A, B).

Example 6

ERRα, ERα and ERβ Proteins are also Expressed in RC Cultures, but Only ERRα and ERα are Detectable in Bone Nodules In Vitro To compare the in vitro localization of ERRα with the ER's in RC cultures, immunocytochemistry was performed with polyclonal antibodies specific for ERα and ERβ (Santa Cruz, Calif.; Shim et al, 1999; Saji et al, 2000; Tremblay et al, 1999) and for ERRα.

Interestingly, ERα was detected in RC cells at all times analysed from early proliferation stages through nodule formation and mineralization with especially strong labeling of osteoblastic cells in nodules (data not shown). ERβ, on the other hand, was more difficult to detect at any time other than in early proliferating cultures; in particular, ERβ was seldom detected in osteoblastic cells in bone nodules (data not shown).

ERR protein was found more widely distributed in RC cell cultures than either ERα or ERβ. ERRα was found in most if not all cells in RC cell cultures from early proliferation stages through mineralized nodule formation. Interestingly, ERRα was found localized in the nucleus as was ERα in mature osteoblasts. ERcx was mainly nuclear from day 2 to day 6 but thereafter was cytoplasmic and nuclear, while ERβ was primarily perinuclear in all cells in which it could be detected (data not shown).

Example 7

ERRα is More Highly and Widely Expressed In Vivo in Fetal Rat Calvaria than ERα and ERβ

To extend the observations made in vitro to bones in vivo, immunocytochemistry was performed on 21 d. fetal rat calvaria sections (data not shown). Consistent with the in vitro results, strikingly different expression patterns were seen for ERRα, ERα and ERβ. ERRα was found in all detectable cohorts of osteoblasts from those associated with nascent bone at the osteogenic front to those in more mature bone trabeculae including remodeling bone. ERα, on the other hand, was not detected in any cells in the suture or osteogenic front, but was detected in some osteoblasts associated with more mature and remodeling bone. ERβ was detected in a pattern virtually reciprocal to that of ERα, i.e., it was present in sutural cells and cells at the osteogenic front, but it was virtually undetectable in osteoblastic cells in more mature and remodeling bone, which is consistent with the mRNA expression in RC cells and the expression in bone nodules. Based on staining intensity, and in keeping with the RT-PCR results, ERRα was more highly expressed than either ERα and ERβ in vivo.

Example 8

ERRα mRNA is also Expressed throughout all Osteoblast Proliferation and Differentiation Stages in Bone Marrow Stromal Cell Cultures In Vitro The calvaria bone, an example of a flat bone, forms by a process of intramembranous ossification, while many other bones form by a process of endochondral ossification. An example of a bone forming by endochondral ossification is the femur, and osteoprogenitor cells also reside in the bone marrow stroma of the femur. ERRα mRNA expression levels were therefore also assessed over a proliferation-differentiation time course by Northern blotting of primary rat bone marrow (RBM) cell populations grown in the presence (+Dex) or absence (−Dex) of dexamethasone (Dex), a stimulator of differentiation in this model as it is in the calvaria-derived cells (data not shown). Under both growth conditions, ERRα mRNA was expressed at all times assessed, including proliferation (day 4), early nodule formation (day 6-9) and nodule mineralization (day 14-17) phases. There was a trend towards increased ERRα expression at early and very late stages, the latter being when mineralized nodules are present, but otherwise levels were relatively constant.

Example 9

Figure 9:
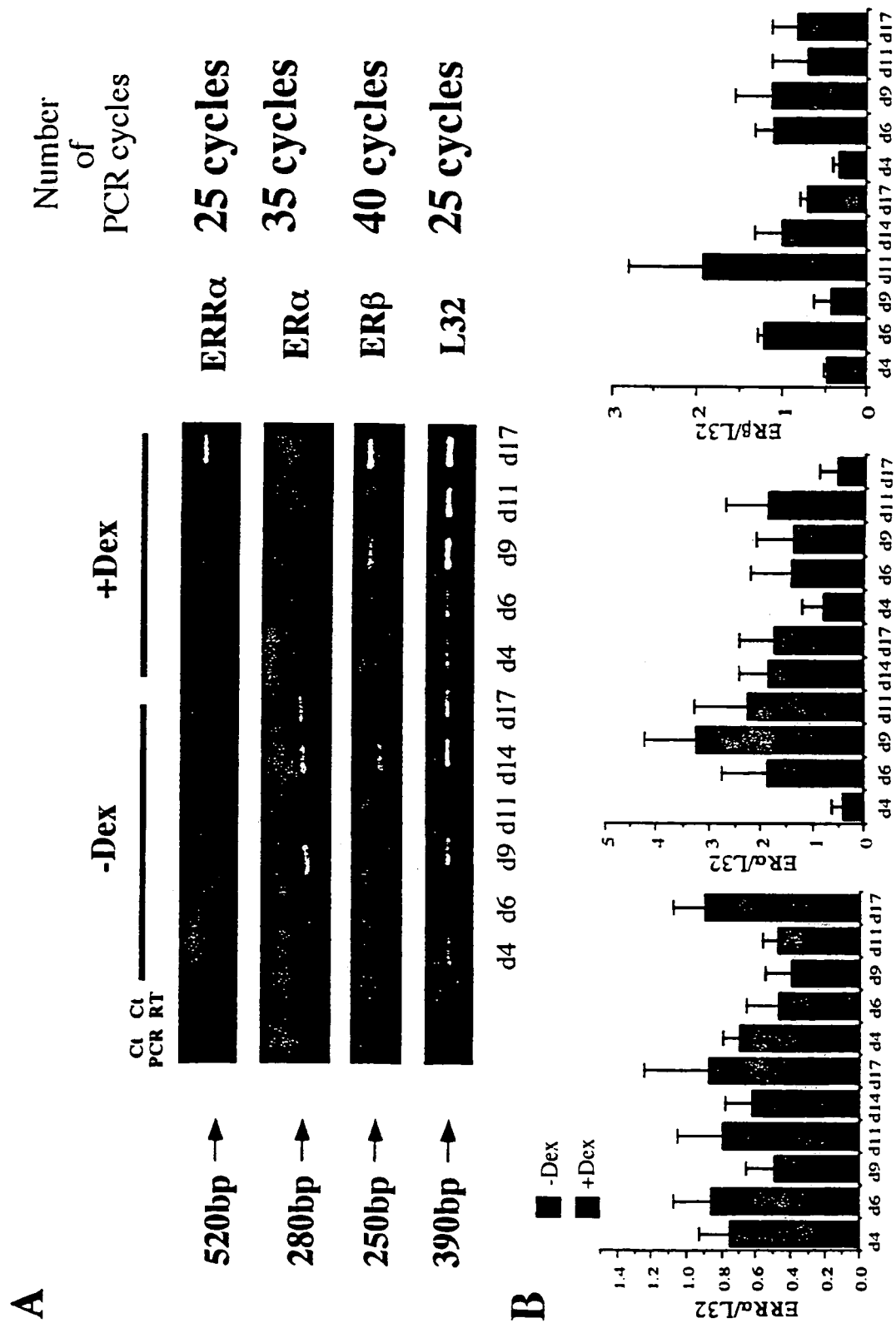
FIG. 9: Expression of ERRα, ERα and ERβ in primary rat bone marrow primary culture (RBM) cells over a proliferation-differentiation time course by RT-PCR in presence (+Dex) or absence (−Dex) of dexamethasone (Dex) during proliferation (day 4-6), early nodule formation (day 9-11) and nodule mineralization (day 14-17) (A). Total RNA was extracted and RT-PCR performed using specific primers for ERRα, ERα and ERβ (A). PCR product was normalized to L32 PCR product (B).

ERRα mRNA is More Highly Expressed in RBM Cell Cultures than either ERα and ERβ mRNA and Expression Patterns Vary The differential expression of ERRα ERα and ERβ mRNA in RC cultures and single bone nodules prompted a comparison of the levels of the three receptors in RBM cultures as well. When RT-PCR was done with primers specific for each of the three receptors. As in the RC model, ERRα was expressed at significantly higher levels than either ERα and ERβ and the two estrogen receptors were themselves present at different levels (i.e., ERRα was easily detected at 25 cycles, while 35 cycles and 40 cycles were required to detect ERα and ERβ respectively) in the RBM model (FIG. 9A, B). In addition, the expression patterns of the three receptors over the proliferation-differentiation time course in RBM cell cultures was strikingly different. Whereas ERRα mRNA expression was relatively uniform over the time course analysed, with or without Dex in the medium, ERα increased late in the proliferation phase (day 4-9) and decreased thereafter, although levels remained higher than at earliest times in −Dex cultures. ERβ also increased during the proliferation phase, but peaked later than ERα, i.e., at day 11 (early 30 differen-tiation phase) and then also decreased. Dex appeared to have a small inhibitory effect on the peak levels reached by both ERα and ERβ.

Example 10

ERRα is also Expressed in Osteoblastic Cells in Fetal and Postnatal Rat Femur

To extend the observations made in vitro to bones in vivo, immunocytochemistry was performed on sections of 21 d. fetal and adult rat femurs (data not shown). Consistent with the in vitro results, ERRα was highly expressed in osteoblasts associated with the growing trabecular and cortical bone. ERRα was also found in the osteocytes present in cortical bone, and in the osteocytes present in the secondary ossification zone, trabecular bone and cortical bone in postnatal (24 days) rat femur; ERRα is also highly expressed in the bone marrow of these animals. These data suggest that ERRα may be involved not only in the formation but also in the maintenance of the bone of the axial skeleton.

Example 11

ERRα Expression is Stimulated by Estrogen, Vitamin D3, and TGFβ and Inhibited by PTH-1-34 in Proliferating RC Cells Cultures.

Figure 10:
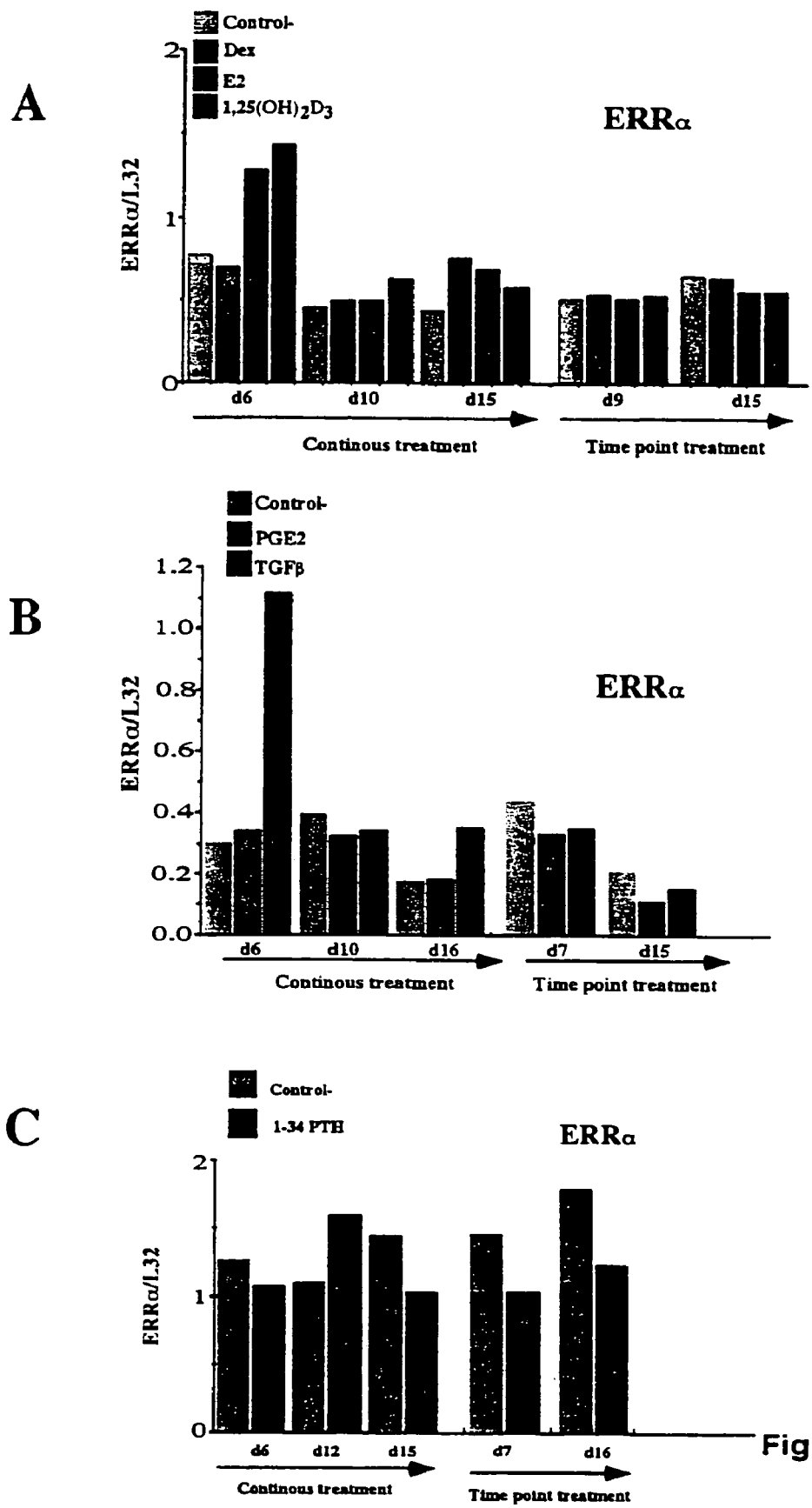
FIG. 10 shows expression of ERRα after normalization with L32 in primary rat bone marrow primary culture (RBM) cells over a proliferation-differentiation time course by Northern blotting in presence of dexamethasone (Dex $10^{-8}$ M), estrogen (E2; $10^{-8}$M), or vitamin $D_3$ (1.250H D3; $10^{-9}$M) (Panel A), or PGE2 ($10^{-9}$ M), TGFβ ($10^{-10}$ M) (Panel B) or 1-34 PTH ($10^{-11}$ M) (Panel C) during proliferation (day 6), early nodule formation (day 10-12) and nodule mineralization (day 15-16). An acute exposure of RC cells for 24 hours at beginning from day 9 (nascent nodule formation) or day 15 (mature nodules present) to either Dex, E2, D3 (A), PGE2, TGFβ (B) or 1-34 PTH (C) were also shown.

To determine whether other hormones or growth factors that influence proliferation and differentiation in RC cell cultures may modulate ERRα levels, we treated RC cells continuously with estrogen (17β-estradiol, E2; $10^{-8}$M), 1,25 (OH)$_2$ vitamin D$_3$ ($10^{-9}$M), PGE$_2$ ($10^{-9}$ M), TGFβ ($10^{-10}$ M) or PTH-1-34 ($10^{-11}$ M). E2 (40% increase), D3 (47% increase) and TGFβ (400%) stimulated expression of ERRα mRNA at day 6, but not later (FIG. 10 A, B). An acute exposure of RC cells to E2, D3 or TGFβ for 24 hours beginning at day 9 (nascent nodule formation) or day 15 (mature nodules present) (E2 and D3) or day 7 and day 15 (TGFβ had no effect on ERRα mRNA levels (FIG. 10, A, B). PTH-1-34 inhibited ERRα at day 6 (15%) and day 15 (26%), but increased (20%) it at day 12 (FIG. 10C). Interestingly, an acute exposure to PTH-1-34 at day 7 or day 16 decreased ERRα by 25% and 33% respectively (FIG. 10C). Neither PGE$_2$ nor Dex had any significant effect on ERRα expression.

Example 12

ERRα Expression is Stimulated By Estrogen in Mouse Femur In Vivo

Figure 11:
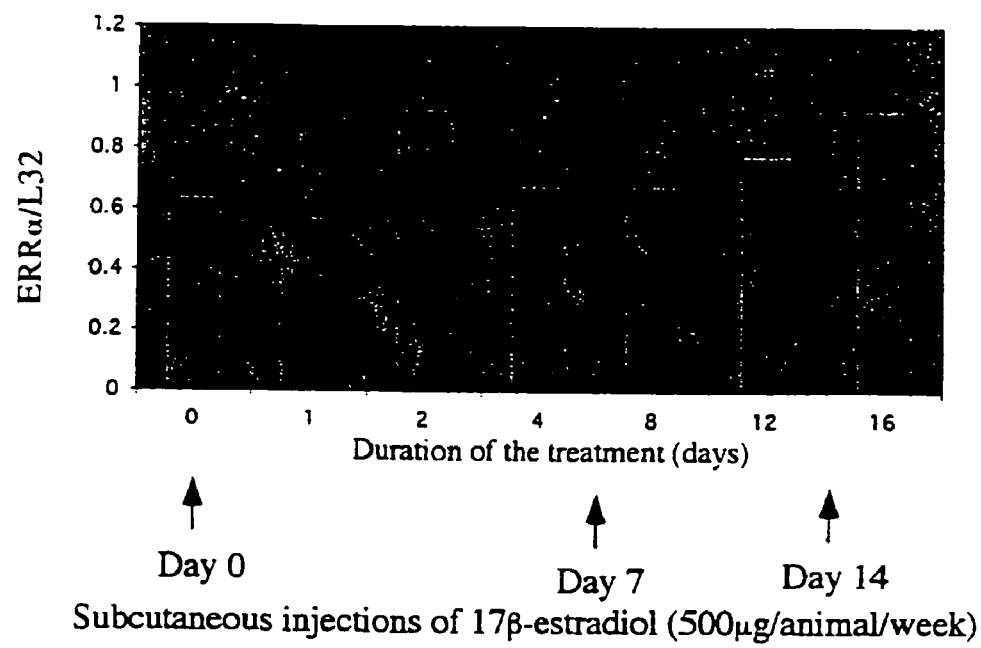
FIG. 11 shows effect of estrogen in vivo on ERRα expression level in mice. Mice were treated once weekly by subcutaneous injection with either vehicle (0.2 ml corn oil) or 500 µg of 17β-estradiol. Total RNA from femur (Panel A) or flushed femur (Panel B) was extracted and RT-PCR performed using specific primers for ERRα. ERRα PCR product was normalized to L32 PCR in femur and flushed femur.
Figure 11:
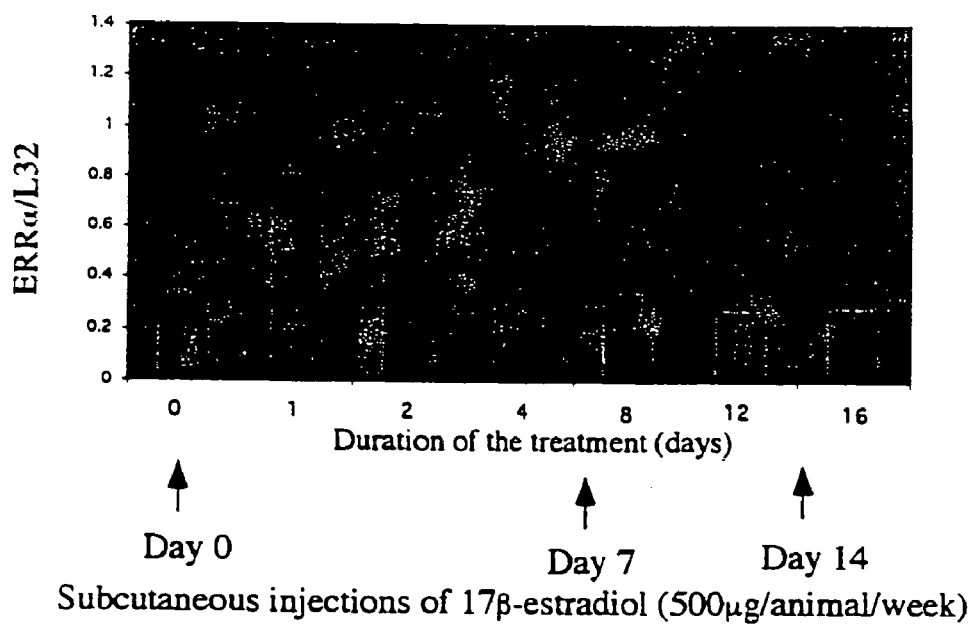

ERRα expression was analysed in samples of mRNA extracted from total femurs or femurs from which bone marrow had been flushed of mice treated with 17β-estradiol at doses known to elicit a large anabolic effect on endosteal bone (Samuels et al, 1999). In samples of total femoral mRNA, E2 had a small stimulatory effect on ERRα mRNA levels that was most evident days 2, 12 and 16 (FIG. 11B). In the mRNA extracted from femurs from which bone marrow had been removed, a marked stimulatory effect of E2 on ERRα levels was evident at day 1, 2 and 4 (FIG. 11A, B).

Example 13

ERRα Expression is Stimulated in Ovariectomized Rats

Figure 12:
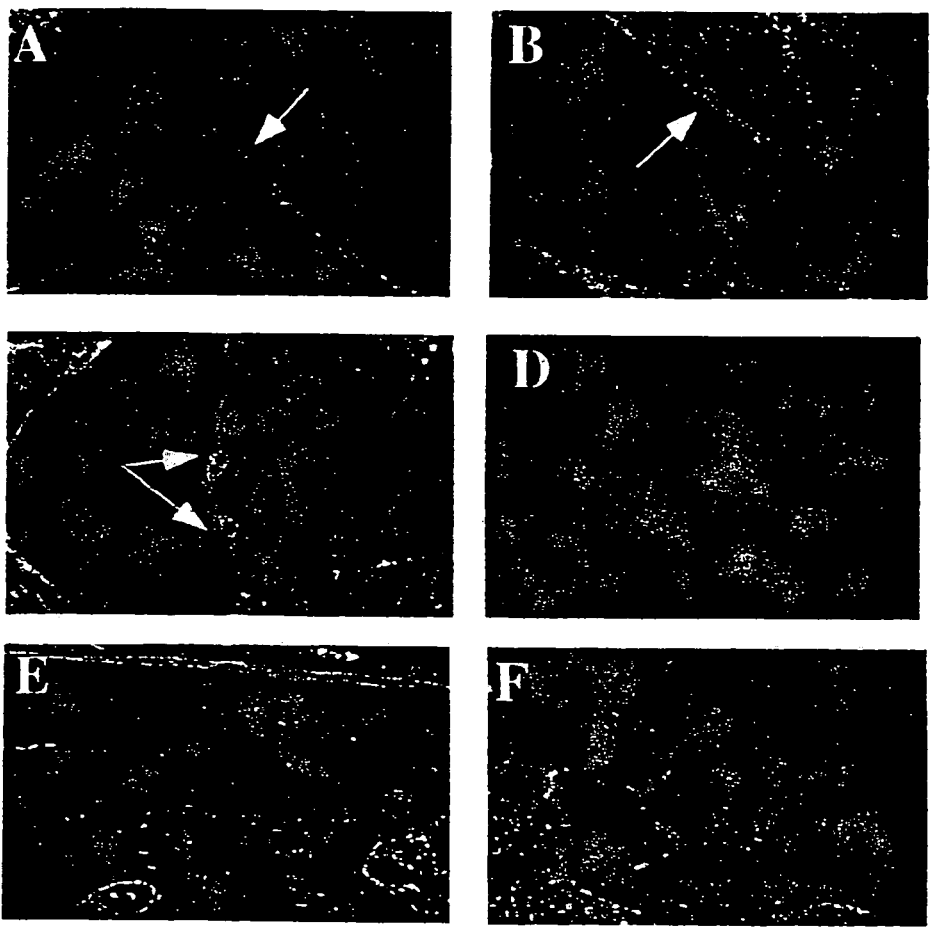
FIG. 12 shows expression of ERRα in a rat model of postmenopausal osteoporosis. Female rats were either ovariectomized (OVX) or sham-operated (Sham). ERRα expression is increased 4 weeks post-surgery in the long bones of OVX, (B, C) versus Sham-operated (A) femurs, but not in calvaria bones (E, OVX vs F, Sham). Active osteoblasts and osteocytes (arrows, A, B) are intensely labeled as are osteoclasts (arrows, C) in sections from the OVX animals. Negative anti-rabbit antibody control is also shown (D).

ERRα is expressed in adult osteocytes in calvaria and long bone, suggesting a function for ERRα during adult life and in diseases of bone, including e.g., those characterized by decreased bone mass such as osteoporosis. Ovariectomized (OVX) rats are a model for human postmenopausal (estrogen loss-induced) osteoporosis. Four weeks after surgery, ERRα expression was increased in osteocytes in the secondary ossification zone and cortical bone (FIG. 12D, H) of long bone and osteoblasts associated with trabecular bone (FIG. 12H, arrows) in OVX compared to sham-operated (FIG. 12A, C, E, G) rats. High expression of ERRα was also found in the abundant osteoclasts in OVX rats (FIG. 12I, arrows). As indicated above, ERRα is expressed in adult calvaria, a site thought not to be affected by OVX, and no striking differences were found in staining intensities in sections from sham versus OVX rats (FIG. 12J, K).

REFERENCES

Aubin, J E, and Liu, F. (1996) in Raisz L G, Rodan G A, Bilezikian, J P (eds) Principles of Bone Biology. Academic Press, San Diego, pp 1-45.

Bain, S D, Bailey, M C, Celino, D L, Lantry, M M, Edwards, M W. (1993) J. Bone and Mineral Research, 8:435-442

Barreback, E. D. (1995) Antibody Engineering, 2d. Edition, Oxford University Press Bellow, C. G., and Aubin, J. E. (1989) Dev. Biol. 133, 8-13

Bellow, C. G., Aubin, J. E., Heersche, J. N. M. and Antosz, M. E. (1986) Calcified Tissue Int., 38: 143-154.

Bonnelye E, J M. Vanacker, X. Desbiens, T. Dittmer, A. Begue, J. Aubin, V. Laudet and B. Fournier. Mol Endocrinol, 11., 1997: 905-916 (a)

Bonnelye E, J M. Vanacker, S. Airic, N. Spruyt, B. Fournier, X. Desbien and V. Laudet.

MOD, 65, 1997: 71-85 (b)

Braidman, J P., Davenport, L K, Howard Carter, D, Selby, P L, Mawer. E B, and Freemont, A J, (1995), L. K. (1995) J. Bone and Mineral Research, 10:74-80

Buckley, M F, Sweeny, K J E, Hamilton, J A, Sini, R L, Manning, D L, Nicholson, R I, DeFazio, A Watts, C K W, Musgrove, E A and Sutherland, R L. (1993) Oncogene 8:2127-2133.

Case, A M and Reid, R L (1998) Arch Intern Med 158 (13): 1405-12.

Chirgwin, J. J., Przbyla, A. E., MacDonald, R. J., and Rutter, W. J. (1979) In Current CP protocols. pp. 4.2.1-4.2.8 John Wiley & Sons, Inc.

Clarke, R, Dickson, R B, and Lippman, M E. (1992) Crit. Rev. Oncol. Hematol. 12:1-23.

Da Silva, J A, Larbre, J P, Seed, M P, Cutolo, M, Villaggio, B, Scott, D L, Willoughby, D A (1994)

J Rheumatol 21 (2):330-7

Denhardt, D. T. and Guo, X. (1993) FASEB J., 7, 1475-1482

Denhardt, D. T and Noda, M (1998) J Cell Biochemistry Supp 30/31:92-102.

Ducy, P, Zhang, R, Geoffroy, V, Ridall, A L and Karsenty, G. (1997) cell 89 (5): 747-54.

Enmark, E and Gustafsson, J-A. (1996) Mol. Endocrinol., 10, 1293-1307

Eriksen, E F, Colvard, D S, Berg, N J, Graham, M L, Mann, K G, Spelsberg, T C, and Riggs, B L 1988 Science 241:84-86

Genovese, C, Rowe, D and Kream, B (1984) Biochemistry 23: 6210-6216.

Giguère V, Yang N, Segui P, Evans R M 1988 Nature 331: 91-94

Green, S., Walter, P., Kumar, V., Krust, A., Bornert, J. M., Argos, P. and Chambon, P. (1986) Nature, 320, 134-139.

Green, S. and Chambon, P (1991) Molecular Mechanisms, Cellular Functions, Clinical Abnormalities. Malcom G. Parker Ed., Academic Press, Harcourt Brace Jovanovich, Publishers, London.

Gronemeyer H, Laudet V 1995 Transcription factors 3: nuclear receptors. Protein profile. 2 : 1173-1308

Grynpas, M D, Huckell, C B, Reichs, K J, Derousseau, C J, Greenwood, C, Kessler M J (1993) J. Bone and Mineral Research 8(8): 909-17

Harris, S A, Tau, K R, Turner, R T and Spelsberg, T C, (1996) in Raisz L G, Rodan G A, Bilezikian, J P (eds) Principles of Bone Biology. Academic Press, San Diego, pp 507-520.

Hines, K. L, Christ, M and S. M Wahl. (1993) Immunomethods. 3:13-22.

Hong, H, Yang, L, and Stallcup, M R (1999) J. Biol. Chem, 274 (32): 22618-22626.

Horwitz et al., (1999), Nat. Med. 5(3): 309-313.

Hoyland, J A, Baris, C, Wood, L, Baird, P, Selby, P L, Freemont, A J and Braidman, I P (1999)

J Patho 188 (3): 294-303

Huiskes, R, Ruimerman, R, Van Lenthe, G A and Janssen, J D. (2000) Nature 405: 704-706.

Johnston, S. D., X. Liu, F. Zuo, T. L. Eisenbraun, S. R. Wiley, R. J. Kraus and J. E. Mertz. Mol. Endocrinol. (1997) 11 : 342-352.

Korach, K. S. (1994). Science, 266, 1524-1527.

Komori, T, Yagi, H, Nomura, S, Yamaguchi, A, Sasaki, K, Deguchi, K, Shimiz, Y, Bronson, R T, Gao, Y H, Inada, M, Sato, M, Okamoto, R, Kitamura, Y, Yoshiki, S, and Kishimoto, T. (1997) cell 89(5):755-64.

Kuiper, G. G. J M., Enmark, E., Pelto-Huikko, M., Nilsson, S. and Gustafsson, J. A. (1996) Proc. Natl. Acad. Sci. USA, 93, 5925-5930.

Komm, B S, Teruening, C M, Benz, D J, Graeme, K A, Gallegos, A, Korc, M, Greene, G L, O'Malley B W and Haussler, M R 1988 Science 241:81-84.

Liu, F., Malaval, L., Gupta, A. K., and Aubin, J. E. (1994) Dev. Biol. 166, 220-234.

Liu, F. and Aubin, J. E. (2000) Submitted.

Malaval, L., Liu, F., Roche, P., and Aubin, J. E. (1999) J. Cell. Biochem., 74, 616-627.

Masi, A T, Freigenbaum, S L and Chatterton, R T (1995) Semin Arthritis Rheum 25 (1):1-27

Noda, M., Yoon, K., Thiede, M., Buenaga, R., Weiss, M., Henthorn, P., Harris, H., and Rodan, G. (1987) J. Bone Miner. Res. 2, 161-164.

Onoe, Y, Miyaura, C, Ohta, H, Nozawa, S and Suda, T, (1997) Endocrinology 138 (10): 4509-4512.

Pacifi, R. (1996) J. Bone Miner. Res., 11, 1043-1051.

Pettersson K, Svensson K, Mattsson R, Carlsson B, Ohlsson R, Berkenstam A 1996 Mech. Dev. 54:211-213

Reddy, S V, Takahashi, S Dallas M, Williams R E, Neckers L and Roodman G D. (1994) J. Bone Miner. Res., 9, 753-757.

Rosner, I A, Goldberg, V M and Moskowitz, R M (1986) Clin Orthop 213:77-83

Sabbah, M, Courilleau, D, Mester, J and Redeuilh, G. (1999) Proc Natl Acad Sci 96:11217-11222.

Saji, S, Jensen, E V, Nilsson, S, Rylander, T, Warner, M and Gustafsson, J A. (2000) Proc Natl Acad Sci 97 :337-342

Sambrook et al., (1989) Molecular Cloning: A Laboratory Manual, Cold Spring Harbor Laboratory Press, Cold Spring Harbor, N.Y.

Samuels, A, Perry, M. J and Tobias, J. H (1999) J. Bone and Mineral Research, 14:178-186.

Shigeta, H., Zuo, W., DiAugustine, R., and Teng, C. T. (1997) J. of Molecular Endocrinology. 19, 299-309.

Shim, W S, DiRenzo, J, DeCaprio, J A, Santen, R J, Brown, M and Jeng, M H (1999) Proc Natl Acad Sci 96:208-213

Sladek, R., J. A. Bader and V. Giguère. (1997) Mol. Cell. Biol. 17 : 5400-5409.

Stein et al. (2000) Cancer 88 (12 Suppl): 2899-2902.

Tremblay, A, Tremblay, G B, Labrie, F and Giguere, V (1999) Mol Cell 3:513-519.

Turksen, K., and Aubin, J. E. (1991) J. Cell Biol. 114, 373-384.

Turksen, K., Bhargava, U., Moe, H. K., and Aubin, J. E. (1992) J. Histochem. Cytochem. 40, 1339-1352.

Turner R T, Riggs B L, Spelsberg T C. (1994). Endocr. Rev. 15: 275-300

Vanacker, J-M., Pettersson, K., Gustafsson, J.-A., and Laudet, V. (1999). EMBO 18, 4270-4279.

Vanacker, J.-M., Delmarre, C., Guo, X. and Laudet, V. (1998) Cell Growth Differ., 9, 1007-1014.

Vega, R B and Kelly, D P. (1997) J. Biol. Chem. 272: 31693-31699.

Wakeling, A. E, Dukes, M and Bowler, J. (1991) Cancer Res. 51: 3867-3873.

Weiss, M J, Cole, D E, Ray, K, Whyte, M P, Lafferty, M A, Mulivor, R A and Harris, H. (1988) Proc Natl Acad Sci 85(20):7666-9.

Wiley S R, Kraus R J, Zuo F, Murray E E, Loritz K, Mertz J E (1993) Genes and Dev. 7: 2206-2219

Windahl, S H, Vidal, O, Andersson, G, Gustafsson, J-A and Ohlsson (1999) J Clin Invest 104:895-901.

Windahl, S H, Norgard, M, Kuiper, G G J M, Gustafsson, J-A and Andersson, G, (2000) Bone 26:117-121.

Xie, W, Hong, H, Yang, N N, Lin, R J, Simon, C M, Stallcup, M R and Evans, R M. Mol Endocrinol (1999) 13(12);2151-62.

Yang N, Shigeta H, Shi H, Teng C T (1996) J. Biol. Chem. 271: 5795-5804

Yang, C and Chen, S (1999) Cancer Res 15; 59 (18): 4519-4524.

Yang, C, Zhou, D and Chen, S (1998) Cancer Res 58: 5695-5700.

Zhang, Z and Teng, T. (2000) J. Biol. Chem J 275: 20837-20846.

Zellar, R. and Rogers, M. (1989). In Current CP protocols. pp. 14.3.1-14.3.14. John Wiley & Sons, Inc.

The invention claimed is:

1. A method for screening a candidate compound for its ability to modulate bone formation comprising:
   (a) providing an assay system for measuring a biological activity of ERRα, wherein the biological activity is selected from the group consisting of osteoblast proliferation, osteoblast differentiation and bone nodule formation; and
   (b) measuring the biological activity of ERRα in the presence or absence of the candidate compound, wherein a change in ERRα activity in the presence of the compound relative to ERRα activity in the absence of the compound indicates an ability to modulate bone formation.

2. The method of claim 1 wherein the change in ERRα activity in the presence of the compound is an increase in activity.

3. The method of claim 2 wherein the increase in ERRα activity in the presence of the compound indicates its potential efficacy as a promoter of bone formation.

4. The method of claim 1 wherein the change in ERRα activity in the presence of the compound is a decrease in activity.

5. The method of claim 4 wherein the decrease in ERRα activity in the presence of the compound indicates its potential efficacy as an inhibitor of bone formation.

6. The method of claim 3 or 5 wherein the assay system for measuring the biological activity of ERRα comprises a rat calvaria cell culture or a bone marrow stromal cell culture.

7. The method of claim 1 wherein the ERRα activity is human ERRα activity.

8. The method of claim 1, wherein the candidate compound is an antisense oligonucleotide.

* * * * *